United States Patent [19]
Wands et al.

[11] Patent Number: 6,071,705
[45] Date of Patent: Jun. 6, 2000

[54] METHOD OF DETECTING NEUROLOGICAL DISEASE OR DYSFUNCTION

[75] Inventors: Jack R. Wands; Jerome Gross, both of Waban; Mehmet Ozturk, Brookline; Suzanne de la Monte, Cambridge, all of Mass.

[73] Assignee: The General Hospital Corporation, Boston, Mass.

[21] Appl. No.: 08/469,629

[22] Filed: Jun. 6, 1995

Related U.S. Application Data

[63] Continuation of application No. 08/055,778, May 3, 1993, abandoned, which is a continuation of application No. 07/451,975, Dec. 20, 1989, abandoned, and a continuation-in-part of application No. 07/287,207, Dec. 21, 1988, abandoned.

[51] Int. Cl.$^7$ .................................................. G01N 33/53
[52] U.S. Cl. ...................... 435/7.1; 435/7.21; 435/7.93; 435/7.94; 435/7.95; 435/40.52; 436/503; 436/544; 436/545; 436/548; 436/63; 436/804; 436/811
[58] Field of Search ........................ 435/7.1, 7.2, 7.21, 435/7.93, 7.94, 475, 40.52; 436/503, 504, 518, 544, 548, 63, 804, 811

[56] References Cited

U.S. PATENT DOCUMENTS 4,666,829   5/1987   Glenner et al. .
5,436,169   7/1995   Iovanna et al. .

OTHER PUBLICATIONS

Schmiegel et al, "Pancreatic Stone Protein in Serum of Patients with Pancreatitis", *Lancet* ii:686–687 (Sep. 20, 1986).
Figarella et al, "Pancreatic stone Protein, Protein X and Thread Protein", *Lancet* i:222–223 (Jan. 24, 1987).
Ozturk et al., *Proc. Natl. Acad. Sci. USA* 86:419–423 (1989).
Glenner et al., *Biochem. Biophys. Res. Comm.* 120:885–890 (1984).
Masters et al., *Proc. Natl. Acad. Sci. USA* 82:4245–4249 (1985).
Kang et al., *Nature* 325:733–736 (1987).
Goldgaber et al., *Science* 235:877–880 (1987).
Tanzi et al., *Science* 235:880–884 (1987).
St George–Hyslop et al., *Science* 235:885–890 (1987).
Broeckhoven et al., *Nature* 329:153–155 (1987).
Gross et al., *J. Clin. Invest.* 76:2115–2126 (1985).
Manetto et al., *Proc. Natl. Acad. Sci. USA* 85:4501–4505 (1988).
Wolozin et al., *Science* 232:648–650 (1986).
Selkoe, *Neurobiology of Aging* 7:425–432 (1986).
Perry et al., *Alterations of the Neuronol Cytoskeleton* in *Alzheimer's Disease* Plenum Press, New York, pp. 137–149 (1987).
Abraham et al., *Cell* 52:487–501 (1988).
De Caro et al., *Biochem. Biophys. Res. Comm.* 87:1176–1182 (1979).
De Caro et al., *Eur. J. Biochem.* 168:201–207 (1987).
Gross et al., *Proc. Natl. Acad. Sci. USA* 82:5627–5631 (1985).
Wischik et al., *Proc. natl. Acad. Sci. USA* 85:4506–4510 (1988).
Wischik et al., *Proc. Natl. Acad. Sci. USA* 85:4884–4888 (1988).
Terazono et al., *J. Biol. Chem.* 263:2111–2114 (1988).
De Caro et al., *Biochem. J.* 222:669–677 (1984).

*Primary Examiner*—Paula K. Hutzell
*Assistant Examiner*—Patricia A. Duffy
*Attorney, Agent, or Firm*—Sterne, Kessler, Goldstein & Fox, P.L.L.C.

[57] ABSTRACT

This invention relates to a method of detecting and diagnosing neurological disease or dysfunction using antibodies against a neurological form of Pancreatic Thread Protein (nPTP). Specifically, this invention is directed to a method of diagnosing Alzheimer's Disease, Down's Syndrome, and other neurological diseases or dysfunctions by using monoclonal antibodies, combination of those monoclonal antibodies or nucleic acid probes, to detect nPTP. The invention also relates to a recombinant DNA molecule encoding PTP and to the substantially pure form of nPTP. The invention additionally relates to a method of diagnosing pancreatic disease using antibodies against Pancreatic Thread Protein.

41 Claims, 12 Drawing Sheets

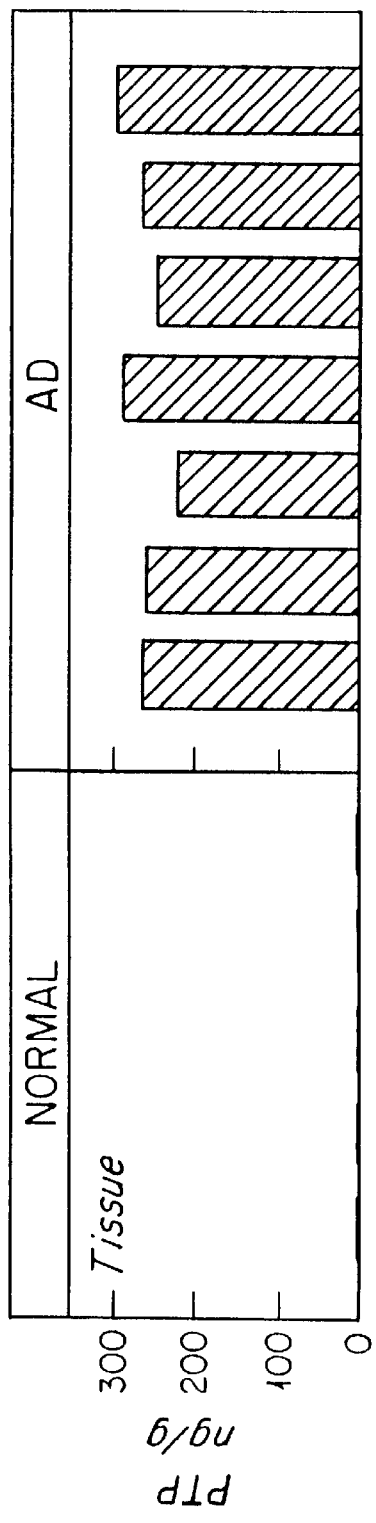
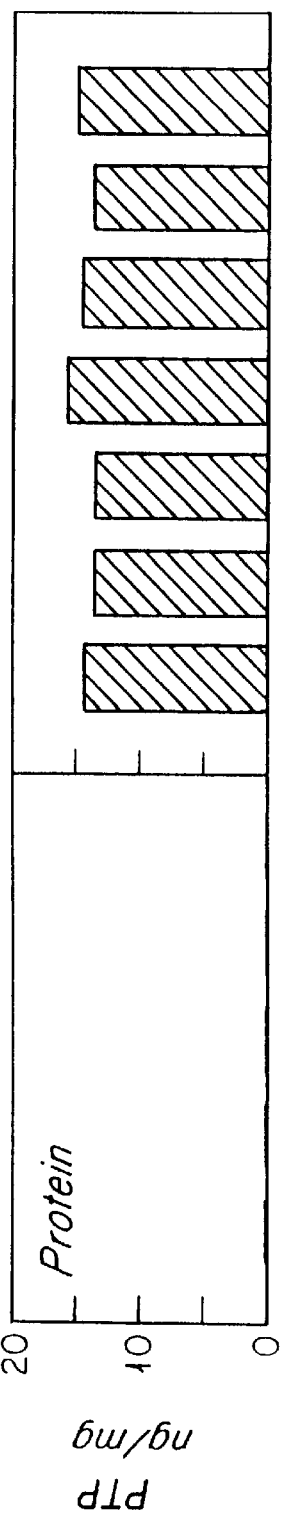
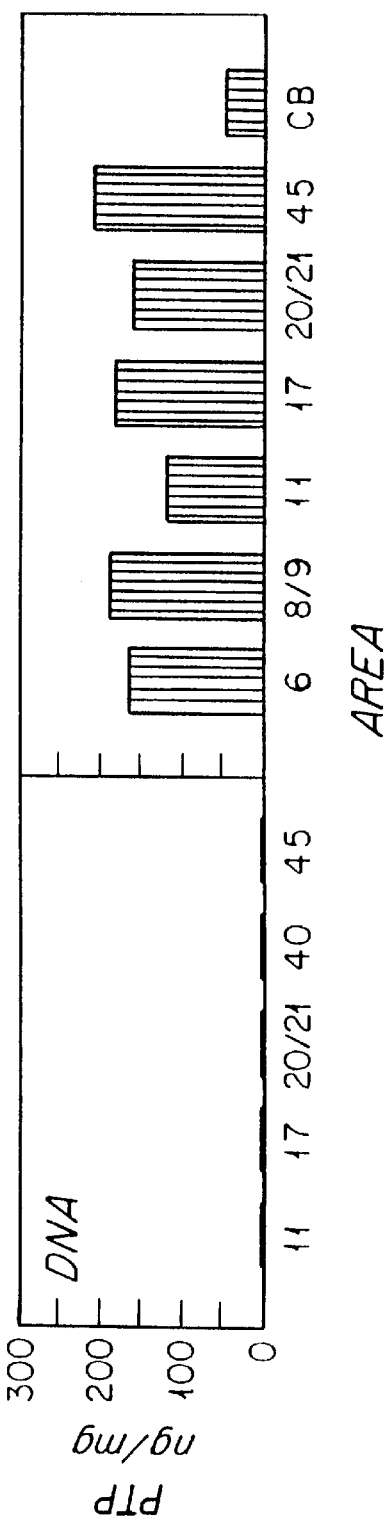
FIG.1A
FIG.1B
FIG.1C

BOVINE PTP: cDNA AND AMINO ACID SEQUENCES

```
GGCACGAGAGCTGCCTCCACACCTCACAGACACAATGCTGCCTTCCCTGGGCCTCCCCAG
                                  M   L   P   S   L   G   L   P   R

ACTGTCCTGGATGCTGCTCTCCTGCCTGATGCTCCTGTCTCAGATCCAAGGGGAAAATTC
 L   S   W   M   L   L   S   C   L   M   L   L   S   Q   I   Q   G   E   N   S

CCAAAAGGAACTGCCATCTGCAAGGATCAGCTGTCCCTCAGGTTCCATGGCCTATAGGTC
 Q   K   E   L   P   S   A   R   I   S   C   P   S   G   S   M   A   Y   R   S

TCACTGCTATGCCTTGTTTAAAACACCCAAAACCTGGATGGATGCAGATATTGCCTGCCA
 H   C   Y   A   L   F   K   T   P   K   T   W   M   D   A   D   I   A   C   Q

GAAGAGGCCCTCGGGACATCTTGTGTCTGTGCTCAGTGGGGCTGAGGAATCCTTCGTGGC
 K   R   P   S   G   H   L   V   S   V   L   S   G   A   E   E   S   F   V   A

CTCCTTGGTTAGGAACAACTTGAACACCCAATCAGACATCTGGATTGGGCTCCATGACCC
 S   L   V   R   N   N   L   N   T   Q   S   D   I   W   I   G   L   H   D   P

CACAGAGGGCTCTGAGGCCAATGCTGGTGGATGGGAATGGATTAGCAATGACGTGCTCAA
 T   E   G   S   E   A   N   A   G   G   W   E   W   I   S   N   D   V   L   N

TTACGTTGCCTGGGAGACAGATCCTGCTGCCATCTCAAGCCCTGGCTACTGTGGGAGTCT
 Y   V   A   W   E   T   D   P   A   A   I   S   S   P   G   Y   C   G   S   L

CTCAAGAAGCTCAGGATATCTCAAGTGGAGAGATCATAACTGCAATTTGAACTTACCCTA
 S   R   S   S   G   Y   L   K   W   R   D   H   N   C   N   L   N   L   P   Y

CGTCTGCAAGTTCACAGACTAGATCAGATGAGAAGTCAGCAGCCTGACTGGTGTGCAACT
 V   C   K   F   T   D   *

GGTGTGCAACTCATCATGGACTTGGAACTAGGGATTCAGACCCACTATGGAAGGGGATAT
TCTTCTCACAGCCCCAACCCAACCACTTCATTCTGACCTTCCCTCCTCCCCAGACTCAAT
TCAGTCTCTTCTGTGTGTTCCATAACCTGACTTTGCAAAGTTCACAATAAAAATATTAGT
TTTCCTCGCC
```

FIG. 9

Primer #1

3'END---TAG TGA ACA GGT CTT CCA AGG TTA CGG ATG TCA AGG ATG ACG

ATG ATG AAA TTA CTT CTG GCA CTC TGG ACC CAA CTA CGT CTA GAG ATA

ACG GCT TTG TAC TTA AGC---5'END

For sequence encoding amino acids:

Ile-Thr-Cys-Pro-Glu-Gly-Ser-Asn-Ala-Tyr-Ser-Ser-Tyr-Cys-Tyr-Tyr-Phe-Met-
Glu-Asp-His-Leu-Ser-Trp-Ala-Glu-Ala-Asp-Leu-Phe-Cys-Gln-Asn-Met-Asn

Primer #2

3'END---TTT TTC TTG GCG GCG ACC GTG ACC TCG TCA CCC AGG GAT CAG

AGG ATG TTC AGG ACC CCG TAA CTT CGG GGT TCG TCG TCA CAA TTA GGA

CCG ATG ACA CAC TCG---5'END

For sequence encoding amino acids:

Lys-Lys-Asn-Arg-Arg-Trp-His-Trp-Ser-Ser-Gly-Ser-Leu-Val-Ser-Tyr-Lys-Ser-
Trp-Gly-Ile-Gly-Ala-Pro-Ser-Ser-Val-Asn-Pro-Gly-Tyr-Cys-Val-Ser-Leu

FIG.11

METHOD OF DETECTING NEUROLOGICAL DISEASE OR DYSFUNCTION

This application is a continuation of application Ser. No. 08/055,778, filed May 5, 1993, now abandoned, which is a continuation of application Ser. No. 07/451,975, filed Dec. 20, 1989, now abandoned, which is a continuation in part of application Ser. No. 07/287,207, filed Dec. 21, 1988, now abandoned.

FIELD OF THE INVENTION

This invention relates to proteins associated with Alzheimer's Disease, Down's Syndrome, neural tube defects and pancreatic disease. The invention further relates to the genes encoding such proteins, immunodiagnostic and molecular diagnostic methods to diagnose these diseases.

Abbreviations

For brevity, the following abbreviations are used throughout this application: Pancreatic Thread Protein (PTP); Neural Pancreatic Thread Protein (nPTP); Immunoradiometric Assay (IRMA); Monoclonal Antibody (mAb); Alzheimer's Disease (AD); Down's Syndrome (DS); Neurofibrillary Tangles (NFTs); and Paired Helical Filaments (PHFs).

BACKGROUND OF THE INVENTION

Neurological Diseases

Alzheimer's Disease (AD) is the most frequent cause of dementia in the United States, affecting over two million individuals each year. It is a degenerative brain disorder characterized clinically by loss of memory, confusion, and gradual physical deterioration. It is the fourth most common cause of death. The etiology of the disease is virtually unknown but has been attributed to various viruses, toxins, heavy metals, as well as genetic defects. The disease is at present incurable.

Until quite recently, AD was thought to account for relatively few of the cases generally classified as senile dementia. Other factors can lead to such a condition, including repetitious mild strokes, thyroid disorders, alcoholism, and deficiencies of certain vitamins, many of which are potentially treatable. It can be appreciated, then, that a diagnostic test specific for AD would be very useful for the clinical diagnosis and proper clinical treatment of subjects presenting with symptoms common to all of these conditions.

The brains of individuals with AD exhibit characteristic pathological accumulations of congophilic fibrous material which occurs as neurofibrillary tangles (NFTs) within neuronal cell bodies, and neuritic (or senile) plaques. NFTs may also be found in the walls of certain cerebral blood vessels. The major organized structural components of NFTs are paired helical filaments (PHFs). Qualitatively indistinguishable amyloid deposits also occur in normal aged brains but in much smaller numbers with restricted topographical distribution.

There has been considerable recent investigative activity regarding the characterization of proteins found in neuritic plaques and NFTs of AD and other neurologic diseases. One of the amyloid proteins initially described by Glenner et al. has been cloned and sequenced (Glenner et al., *Biochem. Biophys. Res. Commun.* 120:1131–1135 (1984); U.S. Pat. No. 4,666,829). The A4 amyloid protein found in neuritic plaques and blood vessels has been determined to be a component of a 695 amino acid precursor; a protein postulated to function as a glycosylated cell surface receptor (Masters et al., *Proc. Natl. Acad. Sci. USA* 82:4245–4249 (1985), Kang et al., *Nature* 325:733–736 (1987)). The gene coding for A4 is located on chromosome 21 (Kang et al., ibid.; Goldgaber et al., *Science* 235:877–880 (1987); Tanzi et al., *Science* 235:880–885 (1987); St. George-Hyslop et al., *Science* 235:885–889 (1987)) but apparently is not linked to the familial form of the disease (Van Broekhoven et al., *Nature* 329:153–155 (1987)). There appears to be little, if any, protein sequence homology between amyloid A4 and β protein, their higher molecular weight precursor, and nPTP described by the present invention (see discussion below) (Gross et al., *J. Clin. Invest.* 76:2115–2126 (1985)).

A number of other proteins thought to be associated with the disease have been described, including Ubiquitin, ALZ-50, microtubular-associated proteins τ and MAP2, and neurofilament protein (see, for example, Manetto et al., *Proc. Natl. Acad. Sci. USA* 85:4502–4505 (1988); Wolozin et al., *Science* 232:648–651 (1986); Selkoe, *Neurobiol. Aging* 7:425–432 (1986); Perry et al., in: *Alterations of the Neuronal Cytoskeleton in Alzheimer's Disease*, Plenum, N.Y., pp 137–149 (1987)). More recently, a serine protease inhibitor called $\alpha_1$-anti-chymotrypsin has been found in AD amyloid deposits (Abraham et al., *Cell* 52:487–501 (1988)).

Until this time, there has been no useful diagnostic test for AD. A definitive diagnosis is possible only postmortem, or during life through a brain biopsy, to reveal the presence of the characteristic plaques, tangles, PHFS, and other cerebrovascular deposits which characterize the disorder. Such an invasive surgical procedure is inherently dangerous and is therefore rarely utilized. As a result, the clinical misdiagnosis of AD is estimated to be approximately 20%–30%.

Down Syndrome (DS) results in mental retardation and is associated with a variable constellation of abnormalities caused by trisomy of at least a critical portion of chromosome 21 in some or all cells. No single physical sign is diagnostic and most stigmata are found in some normal persons. In rare patients, no chromosome abnormalities can be detected by routine cytogenetic analysis. Although DS can generally be detected pre- and post-natally by cytogenetic testing, an alternative diagnostic test which measured a parameter other than a gross karyotypic alteration would be useful in identifying and verifying the presence of DS in a subject, either pre- or post-natally.

Neural tube defects refer to defects which develop in the vertebrate embryo in a tube formed from differentiated middorsal ectoderm. In a developing fetus, the neural tube ultimately gives rise to the brain and spinal cord. Thus, defects in the neural tube often result in severe defects in these organs. For example, such defects could include anencephaly, the absence of the cerebral and cerebellar hemispheres of the brain, spina bifida (absence of vertebral arches of the spinal cord through which the spinal membranes (with or without spinal cord tissue) may protrude), meningocele (protrusion of the brain or spinal cord membranes through a defect in the skull or vertebral column), meningomyelocele (protrusion of the membranes and spinal cord through a defect in the vertebral column), or holoprosencephaly (failure of the forebrain to divide into hemispheres).

A simple prenatal diagnostic test, using amniotic fluid, for example, which could detect neural tube defects would be very useful in determining prenatal or early postnatal treatment such as, for example, immediate postnatal surgical intervention.

Pancreatic and other Diseases

Acute pancreatitis or acute pancreatic injury may be caused by multiple factors including alcohol, penetrating peptic ulcer, gallstones, drugs, trauma, uremia, etc. Diffuse abdominal pain, nausea and vomiting, fever, tachycardia, epigastric tenderness and rigidity are cardinal symptoms and physical findings. Often hemoconcentration and intravascular volume depletion are present. Total serum amylase activity of 3–5 times greater than normal has been the diagnostic anchor for such diseases, despite the lack of specificity of this test. Measurement of serum lipase has also been somewhat helpful in this regard. However, serum amylase and lipase may be elevated in this same range in a variety of serious and life-threatening illnesses, some of which are medical emergencies.

For example, it is well-known that serum lipase and total amylase activities may be elevated in perforated ulcer, intestinal obstruction, intestinal infarction, and renal insufficiency. In these conditions, where no pancreatic injury has occurred, the signs and symptoms may be quite similar to those of acute pancreatitis. The treatment of these extrapancreatic causes of elevated amylase and lipase activities, however, is quite different from that for pancreatitis. For example, surgery for acute pancreatitis is discouraged, whereas failure to perform surgery for intestinal infarction can have lethal consequences. Thus, the search for a more specific diagnostic test of acute and chronic pancreatic injury has great clinical significance.

It is therefore clear that a simple, standardized, and relatively inexpensive assay for diagnosing neural tube defects or pancreatic disease, as well as for specifically detecting DS and AD, would be an immensely useful diagnostic tool for the clinician and researcher alike.

Pancreatic Proteins

Pancreatic Thread Protein (PTP) is found in great abundance in the acinar cells of the pancreas and reaches concentrations of 1–2 mg/ml in normal pancreatic fluid as measured by a monoclonal antibody (mAb)-based immunoradiometric assay (M-IRMA) (Gross et al., *J. Clin. Invest.* 76:2115–2126 (1985)).

PTP in its monomeric form has an apparent molecular weight of approximately 14 kilodaltons (kD), consists of a single polypeptide chain and is rich in aromatic amino acids. The protein has unusual solubility characteristics: it undergoes a pH-dependent fibril formation at pH's between 5.4 and 9.2. The protein forms long "thread like" structures of 7–10 nm (by electron microscopy) when pancreatic fluid is allowed to stand for several hours at 4° C. (Gross et al., *J. Clin. Invest.* 76:2115–2126 (1985)). Thus, PTP represents one of the major secretory products of the exocrine pancreas in man.

Another pancreatic protein called pancreatic stone protein (PSP) has been described by one research group (DeCaro et al., *Biochem. Biophys. Res. Commun.* 87:1176–1182 (1979)). Based on amino acid sequence, PSP appears identical to PTP (DeCaro et al., *J. Biochem.* 168:201–207 (1987)). A similar protein has been identified in bovine pancreas (Gross et al., *Proc. Natl. Acad. Sci. USA* 82:5627–5631 (1985)).

One group of investigators recently found that treatment of highly pure PHFs with pronase removed a 9.5 kD and 12 kD fragment which included the τ microtubular protein (Wischik et al., *Proc. Natl. Acad. Sci. USA* 85:4506–4510 (1988); Wischik et al., *Proc. Natl. Acad. Sci. USA* 85:4884–4888 (1988)). The insoluble core protein remaining following pronase digestion had repeating subunits to which a mAb was made. The mAb bound specifically to the core protein but did not bind the τ protein (Wischik et al., *Proc. Natl. Acad. Sci. USA* 85:4506–4510 (1988)). The solubility characteristics and physical appearance (under electron microscopy) of PTP (Gross et al., *J. Clin. Invest.* 76:2115–2126 (1985)) and the PHF core protein (Wischik et al., *Proc. Natl. Acad. Sci. USA* 85:4506–4510 (1988); Wischik et al., *Proc. Natl. Acad. Sci. USA* 85:4884–4888 (1988)) are similar.

SUMMARY OF THE INVENTION

A need exists for a definitive diagnostic test which can be performed on individuals suspected of having, or being at risk for, AD, DS, and other neurological diseases. The present invention satisfies such needs and provides further advantages.

The manner in which these and other objects are realized by the present invention will be apparent from the summary and detailed description set forth below.

Unless defined otherwise, various terms used herein have the same meaning as is well understood in the art to which the invention belongs. All cited publications are incorporated herein by reference.

Because of the insolubility of PTP at physiologic pH and the physical appearance of the fibrils by electron microscopy, the inventors saw a resemblance of PTP to some of the fibrils observed in neuritic plaques, NFTs, and particularly the PHFs, of AD, leading to their studies which resulted in the present invention.

The inventors have identified, by M-IRMA, high concentrations of a neural form of PTP, referred to as Neural PTP (nPTP) in AD and DS brain. nPTP has been found in all AD brains studied where characteristic neuropathologic changes of the disease exist. The saline-extractable soluble immunoreactivity shares at least three epitopes with the native pancreatic form of PTP and has a molecular weight of approximately 17 to 20 kD.

Quantitative measurements of nPTP immunoreactivity in various regions of AD brains revealed levels varying from 12 to 295 ng/gm tissue (Mean=116 ng/gm tissue) compared to 1–11 ng/gm tissue (Mean=5 ng/gm tissue) in comparable areas of control brains.

Immunocytochemistry performed with mAbs directed against the pancreatic form of PTP demonstrated that nPTP is localized within cells, within fine processes within the neuropil, or is extracellular in both AD and DS brains. Two types of cell contain nPTP: neurons and astrocytes. The affected neurons are the large pyramidal type which typically contain the NFTs well known in AD brain.

That nPTP accumulation within neurons is intrinsically important or integrally related to the evolution of AD lesions is corroborated by the presence of identical patterns of immunolabeling for nPTP in DS brains, but not in control brains. It is important to note that the same structural abnormalities of AD occur in brains of all middle-age individuals with Down's syndrome, whether or not they are demented. There is also a higher incidence of AD in family members of DS patients. Moreover, the regional differences in the densities of nPTP-containing neurons parallels the density distributions of NFTs in both AD and DS. This provides further evidence that nPTP is germane to the pathophysiology of AD. Whether nPTP accumulates within neuronal perikarya, as a result of aberrant cellular metabolism or transport is not yet known. Accordingly, one object of the present invention is to provide a relatively simple, sensitive, accurate, and painless diagnostic method for detecting AD, DS, or other neurological defects which involve incontinence of the bony coverings of central nervous system tissue, such as neural tube defects which would permit the escape of cerebrospinal fluid (CSF).

Another object of the present invention is to provide a highly specific assay for diagnosing and distinguishing AD and DS from other disorders. The assays described by the present invention are non-invasive, thus avoiding the painful and often hazardous removal of brain tissue samples. In view of the immense numbers of individuals potentially afflicted with AD, for example, the assays taught by the present invention will be relatively inexpensive to administer.

An additional object of the present invention is to provide a method for early diagnosis of neural tube defects. Prenatal diagnosis of these defects would allow for corrective actions to be taken prenatally or early postnatally.

Another object of the present invention is to provide a diagnostic method for detecting acute or chronic pancreatic disease, using a combination of antibodies as taught herein.

Furthermore, the assays of the present invention are capable of being reduced to a standardized format, easily and quickly performed.

The present invention additionally pertains to assays for detecting the presence of nPTP in the biological fluids of a human subject using histology, imaging, immunoassays, and the like as diagnostic methods for determining the presence of AD, DS, and neural tube defects, as well as detecting the presence of PTP as a diagnostic method for determining the presence of pancreatic disease.

In particular, the invention includes a method for detecting and quantitating nPTP in a human subject, comprising:
(a) contacting a biological sample from a human subject that is suspected of containing detectable levels of nPTP with a molecule capable of binding to the nPTP; and
(b) detecting the molecule bound to the nPTP.

The invention additionally includes the method as above, wherein the molecule is selected from the group consisting of:
(a) an antibody substantially free of natural impurities;
(b) a monoclonal antibody; and
(c) a fragment of (a) or (b);
(d) a polynucleotide probe derived from the recombinant bovine PTP of this invention; and
(e) a polynucleotide probe derived from recombinant human PTP of this invention.

The invention additionally includes the method as above, wherein the detecting molecule is detectably labeled and where a combination of such molecules is used.

The invention additionally includes a method for determining the presence of a condition in a human subject, said condition including, but not limited to, the group consisting of Alzheimer's Disease, Down's Syndrome, anencephaly, spina bifida, meningocele, meningomyelocele, holoprosencephaly, and pancreatic disease.

The invention additionally includes the method as above, wherein the condition exists as a prenatal condition.

The invention additionally includes a method of diagnosing the presence of AD in a human subject suspected of having AD which comprises:
(a) incubating a biological sample from said subject suspected of containing nPTP with a molecule capable of identifying nPTP; and
(b) detecting the molecule which is bound in the sample, wherein the detection indicates that the subject has AD.

The invention additionally includes a method of diagnosing the presence of DS in a human subject suspected of having DS which comprises:
(a) incubating a biological sample from said subject suspected of containing nPTP with a molecule capable of identifying nPTP; and
(b) detecting the molecule which is bound in the sample, wherein the detection indicates that the subject has DS.

The invention additionally includes a method of diagnosing the presence of pancreatic disease in a human subject suspected of having pancreatic disease which comprises:
(a) incubating a biological sample from said subject, which is suspected of containing PTP, in the presence of a binding molecule capable of identifying PTP; and
(b) detecting the molecule which is bound in the sample, wherein the detection indicates that the subject has pancreatic disease.

The invention additionally includes the methods as above, wherein a biological sample is removed from a human subject prior to contacting the sample with the molecule.

The invention additionally includes the methods as above, wherein detecting any of the molecules bound to the protein is performed by in situ imaging.

The invention additionally includes the methods as above, wherein detecting of any of the molecule bound to the protein is performed by in vitro imaging.

The invention additionally includes the methods as above, wherein the biological sample is reacted with the molecule in a manner and under such conditions sufficient to determine the presence and the distribution of the protein.

The invention additionally includes the methods as above, wherein a detectably labeled binding molecule is administered to a human subject.

The invention additionally includes the methods as above, wherein the molecule is bound to the protein in vivo.

The invention additionally includes nPTP substantially free of any natural impurities with molecular weights of less than about 17 kD daltons, the nPTP having a molecular weight of about 17–20 kD. However, larger molecular weight forms may be detected and isolated with more vigorous extraction procedures.

The invention also includes a method for recovering nPTP substantially free of natural impurities which includes, but is not limited to, the following steps:
(a) recovering crude nPTP from a biological sample;
(b) subjecting the crude nPTP from step (a) to ion-exchange chromatography to obtain partially purified fractions of nPTP;
(c) subjecting the partially purified fractions of nPTP from step (b) to molecular sieve chromatography to obtain nPTP; and
(d) purifying nPTP to homogeneity by subjecting the nPTP from step (c) to gel chromatography to obtain nPTP substantially free of natural impurities with molecular weights of less than about 17 kD, said nPTP having a molecular weight of about 17–20 kD daltons.

The invention also includes the method as above, further comprising:
(e) subjecting the purified nPTP obtained in step (d) to affinity chromatography to obtain highly purified nPTP substantially free of natural impurities with molecular weights of less than about 17 kD, the nPTP having a molecular weight of about 17–20 kD.

The invention is particularly directed to a diagnostic method for determining the presence of AD in a human subject by detecting and measuring the concentration of nPTP by immunoassay, comprising:
(a) reacting a biological sample from a subject suspected of containing nPTP with an antibody or antibodies specific to nPTP;
(b) monitoring the reaction of step (a) to determine whether the antibodies have bound to nPTP, the concentration of nPTP indicating whether the subject has AD.

The invention is also directed to a diagnostic method for determining the presence of DS in a human subject by detecting and measuring the concentration of nPTP by immunoassay, comprising:

(a) reacting a biological sample from a subject suspected of containing nPTP with an antibody or antibodies specific to nPTP;

(b) monitoring the reaction of step (a) to determine whether the antibodies have bound to nPTP, the concentration of nPTP indicating whether the subject has DS.

Additionally, the invention is particularly directed to a diagnostic method for determining the presence of pancreatic disease in a human subject by detecting and measuring the concentration of PTP by immunoassay, comprising:

(a) reacting a biological sample from a subject suspected of containing PTP with an antibody or antibodies specific to PTP;

(b) monitoring the reaction of step (a) to determine whether the antibodies have bound to nPTP, the concentration of PTP indicating whether the subject has pancreatic disease.

The present invention also particularly relates to the diagnostic methods recited above, wherein the immunoassay comprises two different antibodies bound to a solid phase support combined with a third different detectably labeled antibody in solution.

DESCRIPTION OF THE FIGURES

FIG. 1. Comparison of nPTP concentrations in various regions of normal and AD brain. High levels of nPTP were found in all areas of AD brain tested. Alternate expression of nPTP immunoreactivity as ng/mg weight (top), ng/mg protein (middle), and ng/mg DNA (bottom) did not alter the magnitude of values observed in AD brain.

FIG. 9. cDNA and deduced amino acid sequence of bovine PTP. A bovine pancreatic cDNA library ligated into the EcoRI site of the λZAP cloning vectors (Lang) was screened with polyclonal antibody to purified PTP. Twenty-seven clones with insert sizes between 0.65 and 0.9 kB were identified from 6×10$^4$ plaques. A probe prepared from the 2-1 insert hybridized with 20 of the 27 clones by Southern analysis. The 2-1 insert was sequenced by the dideoxynucleotide chain-termination method using plasmid DNA and T7 polymerase (Ausubel, F. M., et al., Current Protocols in Molecular Biology, Wiley & Sons, New York, 1989, Chapter 7.4). This full-length clone has one continuous open reading frame beginning from the first methionine codon and a polyadenylation signal. The deduced amino acid sequence shares 98% identity with, the amino acid sequence of the A and B chains of bovine PTP (Gross et al., J. Clin. Invest. 76:2115–2126 (1985)). Additional information derived from the cDNA include the presence of a 36-residue hydrophobic leader sequence, potential cleavage sites at residues 36, 138, and 6 possible phosphorylation sites.

FIG. 11. Nucleotide sequence of two oligonucleotide probes used to probe for human PTP, and the sequence of encoded amino acids.

DESCRIPTION OF THE PREFERRED EMBODIMENTS

Figure 2A:
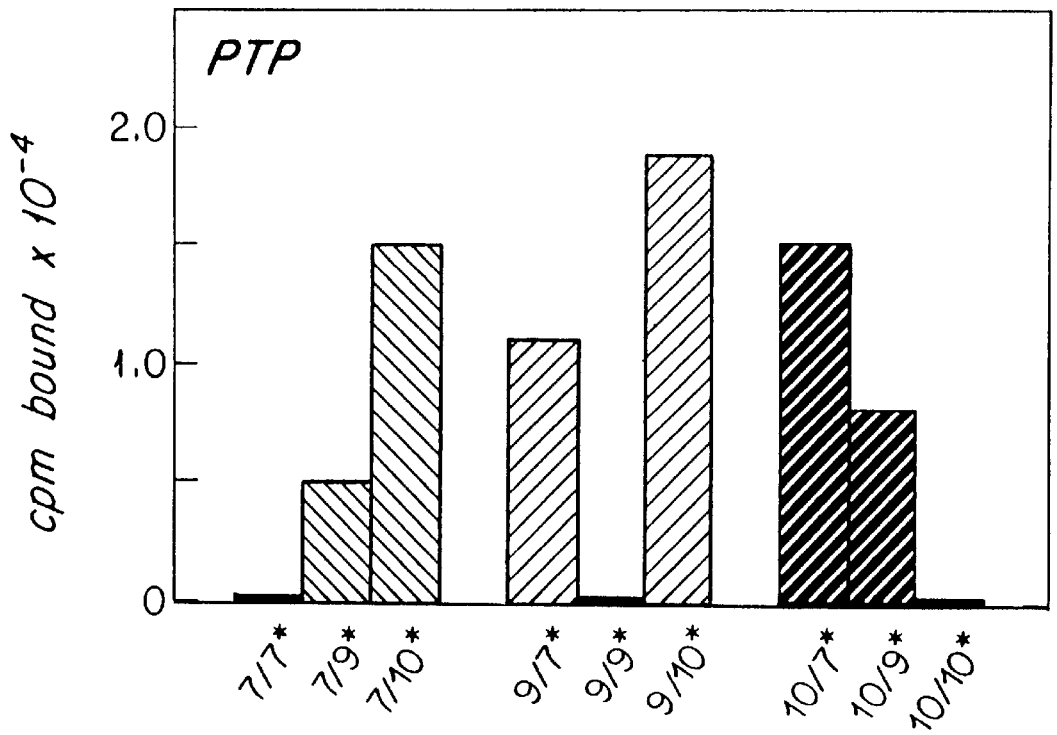
FIG. 2. Epitope mapping of PTP derived from pancreatic fluid compared to PTP in Area 20/21 of AD brain. The mAbs designated 7, 9 and 10 were bound to a solid support and incubated with PTP or AD brain extract. Immunoreactivity was detected with $^{125}$I-labeled mAbs 7*, 9*, and 10* (see Gross et al., J. Clin. Invest. 76:2115–2126 (1985)). All three epitopes present on the native pancreatic form of PTP were found in AD brain extracts.

This invention is based upon the inventors unexpected discovery in brain tissue of PTP immunoreactivity using a combination of mAbs, each directed against a different epitope of the native pancreatic PTP. Elevated levels of this PTP immunoreactivity was detected in brains of AD and DS patients.

Genetic Sequences

This invention is also directed to polynucleotide sequences encoding human pancreatic and neural forms of PTP, to vectors containing these sequences, and to specific oligonucleotide or polynucleotide probes capable of hybridizing with these sequences.

Techniques for synthesizing such oligonucleotides are disclosed by, for example, Wu, R., et al., *Prog. Nucl. Acid. Res. Molec. Biol.* 21:101–141 (1978)). Procedures for constructing recombinant molecules in accordance with the above-described method are disclosed by Maniatis, T., et al., In: *Molecular Cloning: A Laboratory Manual*, Cold Spring Harbor Press, Cold Spring Harbor, N.Y. (1984), which reference is herein incorporated by reference.

Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). Using the genetic code, one or more different oligonucleotides can be identified, each of which would be capable of encoding the PTP or nPTP protein. The probability that a particular oligonucleotide will, in fact, constitute the actual xxx-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding the PTP or nPTP peptide sequences is identified.

Although occasionally an amino acid sequence may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding the PTP or nPTP protein or peptide fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the PTP or nPTP gene (Maniatis, T., et al., *Molecular Cloning A Laboratory Manual*, Cold Spring Harbor Press, Cold Spring Harbor, N.Y. (1982)).

A suitable oligonucleotide, or set of oligonucleotides, which is capable of encoding a fragment of the PTP or nPTP gene (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing the PTP or nPTP. Single stranded oligonucleotide molecules complementary to the "most probable" PTP or nPTP peptide encoding sequences can be synthesized using procedures which are well known to those of ordinary skill in the art (Belagaje, R., et al., *J. Biol. Chem.* 254:5765–5780 (1979); Maniatis, T., et al., In: *Molecular Mechanisms in the Control of Gene Expression*, Nierlich, D. P., et al., Eds., Acad. Press, NY (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Maniatis, T., et al. (In: *Molecular Cloning, A Laboratory Manual*, Cold Spring Harbor Laboratories, Cold Spring Harbor, N.Y. (1982)), and by Haymes, B. D., et al. (In: *Nucleic Acid Hybridization, A Practical Approach*, IRL Press, Washington, D.C. (1985)), which references are herein incorporated by reference.

Techniques such as, or similar to, those described above have successfully enabled the cloning of genes for human aldehyde dehydrogenases (Hsu, L. C., et al., *Proc. Natl. Acad. Sci. USA* 82:3771–3775 (1985)), fibronectin (Suzuki, S., et al., *Eur. Mol. Biol. Organ. J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:8715–8719 (1985)).

In a alternative way of cloning the PTP or nPTP gene, a library of expression vectors is prepared by cloning DNA or, more preferably, cDNA (from a cell capable of expressing PTP or nPTP) into an expression vector. The library is then screened for members capable of expressing a protein which binds to anti-PTP antibody, and which has a nucleotide sequence that is capable of encoding polypeptides that have the same amino acid sequence as PTP or nPTP, or fragments thereof. In this embodiment, DNA, or more preferably cDNA, is extracted and purified from a cell which is capable of expressing PTP or nPTP. The purified cDNA is fragmented (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing PTP or nPTP in order to produce a prokaryotic genomic expression vector library. Procedures for preparing cDNA and for producing a genomic library are disclosed by Maniatis, T., et al. (*Molecular Cloning: A Laboratory Manual*, Cold Spring Harbor Press, Cold Spring Harbor, N.Y. (1982)).

The expression of PTP or nPTP protein or peptide in prokaryotic or eukaryotic hosts according to this invention requires the presence of a promoter which is "operatively linked" to the nucleotide sequence coding for the protein of interest.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be "operably linked" it is not necessary that two sequences be immediately adjacent to one another.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)* 81:2035–2039 (1984)) polymerases; the $P_R$ and $P_L$ promoters of bacteriophage λ. (*The Bacteriophage Lambda*, Hershey, A. D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trP, recA, heat shock, and lacZ promoters of *E. coli*; the α-amylase (Ulmanen, I., et al., *J. Bacteriol.* 162:176–182 (1985)) and the σ-28-specific promoters of *B. subtilis* (Gilman, M. Z., et al., *Gene* 32:11–20 (1984)); the promoters of the bacteriophages of *Bacillus* (Gryczan, T. J., In: The Molecular *Biology of the Bacilli*, Academic Press, Inc., NY (1982)); Streptomyces promoters (Ward, J. M., et al., *Mol. Gen. Genet.* 203:468–478 (1986)); the int promoter of bacteriophage λ; the bla promoter of the β-lactamase gene of pBR322, and the CAT promoter of the chloramphenicol acetyl transferase gene of pPR325, etc. Prokaryotic promoters are reviewed by Glick, B. R., (*J. Ind. Microbiol.* 1:277–282 (1987)); Cenatiempo, Y. (*Biochimie* 68:505–516 (1986)); Watson, J. D. et al. (In: *Molecular Biology of the Gene*, Fourth Edition, Benjamin Cummins, Menlo Park, Calif. (1987)); and Gottesman, S. (*Ann. Rev. Genet.* 18:415–442 (1984)). Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); and the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)). All of the above listed references are incorporated by reference herein.

Strong promoters are the most preferred promoters of the present invention. Examples of such preferred promoters are those which recognize the T3, SP6 and T7 polymerase promoters; the $P_L$ promoter of bacteriophage λ; the recA promoter and the promoter of the mouse metallothionein I gene. The most preferred promoter is one which is capable of recognizing the T7 polymerase promoter. The sequences of such polymerase recognition sequences are disclosed by Watson, J. D. et al. (In: *Molecular Biology of the Gene*, Fourth Edition, Benjamin Cummins, Menlo Park, Calif., (1987)).

Nucleic Acid Probes and Hybridization Assays

The nucleic acid probes of this invention comprise sequences identical to, or homologous to, the sequence of nPTP or its fragments.

The desired nucleotide probe sequence may include flanking naturally occuring nucleotides as well, with the proviso that these flanking nucleotides may not be present in such numbers as to alter the hybridization specificity of the DNA or RNA sequence. Typically, the probe sequence will contain at least 18 nucleotides. Thus, further intended within the scope of this invention are any and all polynucleotides containing, as a minimum, 18 members that are part of or homologus to probes to nPTP.

These probes can be either in DNA or in RNA form. They can be obtained by known and published isolation and digestion procedures (supra) or synthesized by standard methods. The probe may be obtained from mRNA, from cDNA obtained by reverse transcription of mRNA with reverse transcriptase or by cleavage of the genome, conveniently by endonuclease digestion, followed by cloning of the gene or gene fragment in accordance with known techniques. See, for example, Kornberg, *DNA Replication*, W. H. Freeman & Co, San Francisco, 1980, pp. 670–679. Alternatively, the probe may be synthesized according to the technique described by Merrifield, *J.M. Chem. Soc.* 85:2149 (1962). After isolation of the DNA fragment, the fragment may be used for preparation of the probe.

The probe can be by itself or may be part of a plasmid, such as, for example, plasmid pBR322.

The probe is detectably labelled, the labels of most utility being radioactive atoms, enzymes, chromophores, biotin/avidin, or the like. A more complete discussion of nucleic acid hybridization technology may be found in Huang, E. S. et al. 6:457–497 (1977), incorporated by reference herein. Oligonucleotide probe technology is also disclosed by Szostak, J. W. et al., *Meth. Enzymol.* 68:419–428 (1979), also incorporated by reference herein.

The polynucleotide or oligonucleotide probe may be labeled with an atom or inorganic radical, most commonly using radionuclides, but also perhaps heavy metals. In some situations, it may also be possible to employ an antibody which will bind specifically to the probe hybridized to the target DNA.

Most commonly, a radioactive label is employed, suitable radioactive labels including $^{32}P$, $^{3}H$, $^{14}C$, $^{125}I$, or the like. Any radioactive label may be employed which provides for an adequate signal and has a sufficient half-life. Other labels include ligands, fluorescers, chemiluminescers, enzymes, antibodies, and the like.

In one technique of labelling, *E. coli* DNA polymerase I may be utilized to add nucleotide residues to the 3'-hydroxy terminus that is created when one strand of a double-stranded DNA molecule is nicked. In addition, the enzyme, by virtue of its 5' to 3' exonucleolytic activity, may remove nucleotides from the 5' side of the nick. The elimination of nucleotides from the 5' side and the sequential addition of nucleotides to the 3' side results in the formation of the nick (nick translation) along the DNA (Kelley et al., *J. Biol. Chem.* 245:39 (1970)). By replacing the preexisting nucleotides with highly radioactive nucleotides, it is possible to prepare a labelled probe with a specific activity well in excess of $10^8$ cpm/μg (Rigby, P. W. J. et al., *J. Mol. Biol.* 113:237 (1977)).

Probes may be labelled to high specific activity using either $^3$H-thymidine triphosphate or alpha-$^{32}$P-deoxynucleotide triphosphates by such nick translation (Rigby et al., supra).

In testing a tissue sample for nPTP, RNA can be isolated from tissue by sectioning on a cryostat and lysing the sections with a detergent such as SDS and a chelating agent such as EDTA, optionally with overnight digestion with proteinase K (50 μg/ml). Protein is removed by phenol and chloroform extractions, and nucleic acids are precipitated with ethanol. RNA is isolated by chromatography on an oligo dT column and then eluted therefrom. Further fractionation can also be carried out.

A number of techniques for molecular hybridization are used for the detection of DNA or RNA sequences in tissues; each has certain advantages and disadvantages. When large amounts of tissue are available, analysis of hybridization kinetics provides the opportunity to accurately quantitate the amount of DNA RNA present, as well as to distinguish sequences that are closely related but not identical to the probe, and determine the percent homology.

Reactions are run under conditions of hybridization (Tm-25° C.) in which the rate of reassociation of the probe is optimal (Wetmur, J. G. et al., *J. Mol. Biol.* 31:349–370 (1968)). The kinetics of the reaction are second-order when the sequences in the tissue are identical to those of the probe; however, the reaction exhibits complex kinetics when probe sequences have partial homology to those in the tissue (Sharp, P. A. et al., *J. Mol. Biol.* 86:709–726 (1974)).

The concentration of probe to cell RNA is determined by the sensitivity desired. To detect one transcript per cell would require about 100 pg of probe per μg of total cellular DNA or RNA. The nucleic acids are mixed, denatured, brought to the appropriate salt concentration and temperature, and allowed to hybridize for various periods of time. The rate of reassociation can be determined by quantitating the amount of probe hybridized either by hydroxyapatite chromatography (Britten, R. J. et al., *Science* 161:529–540 (1968)) or SI nuclease digestion (Sutton, W. D., *Biochim. Biophys. Acta* 240:522–531 (1971)).

A more flexible method of hybridization is the Northern blot technique. This technique offers variability in the stringency of the hybridization reaction, as well as determination of the state of the retroviral sequences in the specimen under analysis. Cell RNA is denatured in situ with alkali, neutralized and transferred to a nitrocellulose membrane.

After washing, the membrane is baked under vacuum and prehybridized in 10X Denhardts solution (0.2% each of Ficoll, bovine serum albumin, polyvinylprollidone) in 4X SSC (SSC=0.15M NaCl, 0.05M sodium citrate) containing 50 μg/ml sonicated and denatured salmon sperm DNA for four hours at 60° C. Stringent hybridization or nonstringent hybridization can be carried out. Membranes are washed extensively in 4X SSC at 52° C., air dried and detected.

A major consideration associated with hybridization analysis of DNA or RNA sequences is the degree of relatedness the probe has with the sequences present in the specimen under study. This is important with the blotting technique, since a moderate degree of sequence homology under nonstringent conditions of hybridization can yield a strong signal even though the probe and sequences in the sample represent non-homologous genes.

The particular hybridization technique is not essential to the invention, any technique commonly used in the art being within the scope of the present invention. Typical probe technology is described in U.S. Pat. No. 4,358,535 to Falkow et al., incorporated by reference herein.

The labelled probes, as described above, provide a general diagnostic method for detection of nPTP in tissue. The method is reasonably rapid, has a simple protocol, has reagents which can be standardized and provided as commercial kits, and allows for rapid screening of large numbers of samples.

In one method for carrying out the procedure, a clinical isolate containing RNA transcripts is fixed to a support. The affixed nucleic acid is contacted with a labelled polynucleotide having a base sequence complementary or homologous to the coding strand of the nPTP gene.

The hybridization assays of the present invention are particularly well suited for preparation and commercialization in kit form, the kit comprising a carrier means compartmentalized to receive one or more container means (vial, test tube, etc.) in close confinement, each of said container means comprising one of the separate elements to be used in the hybridization assay.

The presence of nPTP RNA is determined by the variation in the appearance and/or quantity of probe-related RNA in tested tissue.

Polypeptides

The invention is also directed to nPTP substantially free of natural contaminants, or substantially pure nPTP, and its functional derivatives or fragments.

The terms "functional derivatives" or "fragments" are intended to include the "variants," "analogues," or "chemical derivatives" of the molecule. A "fragment" of a molecule such as PTP or nPTP is meant to refer to any polypeptide subset of that molecule. A "variant" of a molecule such as PTP or nPTP is meant to refer to a naturally occurring molecule substantially similar to either the entire molecule, or a fragment thereof. An "analogue" of a molecule such as PTP or nPTP is meant to refer to a non-natural molecule substantially similar to either the entire molecule or a fragment thereof.

A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in *Remington's Pharmaceutical Sciences* (1980) and will be apparent to those of ordinary skill in the art.

The term "nPTP" refers to a protein substantially free of natural impurities, with a molecular weight of approximately 17–20 kD which is found in the brains of AD-afflicted individuals at a concentration of approximately 12–295 ng/mg tissue wet weight, and in biological fluids (such as CSF) at a concentration above approximately 20 ng/ml. It is found in biological fluids, such as amniotic fluid, at a concentration above approximately 200 ng/ml when a subject is suffering from a neural tube defect. It is demonstrable in subjects afflicted with DS by immunohistochemical staining. It was also found in the brains of normal individuals, but in greatly reduced concentrations and in far fewer cells. (See FIGS. 3 and 5.)

nPTP is similar to the pancreatic form of PTP, found in the acinar cells of the pancreas, and having a molecular weight of approximately 14 kD (see above).

The nPTP molecule disclosed herein is said to be "substantially free of natural impurities" or "substantially pure" if preparations which contain it are substantially free of contaminants or materials with which this molecule is normally and naturally found, for example, proteinaceous, carbohydrate, or lipid impurities having molecular weights of less than about 17,000 daltons.

The term is further meant to describe a molecule which is homogeneous by one or more purity or homogeneity characteristics used by those of skill in the art. For example, a substantially pure nPTP will show constant and reproducible characteristics within standard experimental deviations for parameters such as the following: molecular weight, chromatographic migration, amino acid composition, amino acid sequence, blocked or unblocked N-terminus, HPLC elution profile, biological activity, and other such parameters. The term, however, is not meant to exclude artificial or synthetic mixtures of the factor with other compounds.

The nPTP protein or fragment of this invention may be obtained by expression from recombinant DNA as described above. Alternatively, nPTP may be purified from biological material.

For purposes of the present invention, one method of purification which is illustrative, without being limiting, consists of the following steps:

A first step in the purification of nPTP includes extraction of the nPTP fraction from a biological sample, such as brain tissue, in buffers, with or without solubilizing agents such as urea, formic acid, detergent, or thiocyanate.

A second step includes subjecting the solubilized material to ion-exchange chromatography on Mono-Q or Mono-S columns (Pharmacia). Similarly, the solublized material may be separated by any other process wherein molecules can be separated according to charge density, charge distribution and molecular size, for example. Elution of the nPTP from the ion-exchange resin are monitored by M-IRMA on each fraction. Immunoreactive peaks are then dialyzed, lyophilized, and subjected to molecular sieve, or gel chromatography.

Molecular sieve or gel chromatography is a type of partition chromatography in which separation is based on molecular size. Dextran, polyacrylamide, and agarose gels are commonly used for this type of separation. One useful gel for the present invention is Superose 12 (Pharmacia). However, other methods, known to those of skill in the art may be used to effectively separate molecules based on size.

A fourth step in a purification protocol for nPTP includes analyzing the immunoreactive peaks by sodium dodecyl sulfate-polyacrylamide gel electrophoresis (SDS-PAGE), a further gel chromatographic purification step, and staining, such as, for example, silver staining.

A fifth step in a purification method includes subjecting the nPTP obtained after SDS-PAGE to affinity chromatography, or any other procedure based upon affinity between a substance to be isolated and a molecule to which it can specifically bind. For further purification of nPTP, affinity chromatography on Sepharose conjugated to anti-PTP mAbs 7, 9 and 10 can be used. Alternative methods, such as reversephase HPLC, or any other method characterized by rapid separation with good peak resolution are useful.

In a specific embodiment of the present invention, purification of nPTP includes the following steps:

(a) Solubilization of nPTP from brain: nPTP is extracted with phosphate buffered saline (PBS) alone or in the presence of solubilizers such as urea, formic acid, detergent or thiocyanate;

(b) Ion exchange chromatography on Mono-Q: Protein extract is loaded in the column on 25 mM Tris (pH 9.0) and retained fractions are eluted by a gradient of 0–500 mM NaCl in the same buffer. Immunoreactive peaks are localized by testing with the IRMA for PTP, pooled and dialyzed against distilled water, and lyophilized;

(c) The lysate is solubilized in a minimal volume of 100 mM Tris (pH 9.0) and loaded onto a Superose 12 column. The nPTP peak is localized by IRMA and lyophilized;

(d) The purity of nPTP was tested by SDS-PAGE with silver staining. If necessary, the final product can be purified further by affinity chromatography, according to step (e), below;

(e) CNBr-activated Sepharose is conjugated with purified anti-PTP mAbs (7, 9 or 10) to obtain an affinity matrix. Partially purified nPTP is loaded onto a column containing the affinity matrix at neutral pH and eluted with citrate buffer (pH 2.2). After extensive dialysis against distilled water, the final product is lyophilized and dissolved in a minimal volume of distilled water. This step could alternatively include purification using reverse-phase HPLC (Novapac C18, Waters).

It will be appreciated that other purification steps may be substituted for the preferred method described above. Those of skill in the art will be able to devise alternate purification schemes without undue experimentation.

Methods of Detecting PTP and nPTP

This invention is directed towards methods of detecting AD, DS, various neural tube defects, and pancreatic disease in a human subject, utilizing the nucleic acid probes hybridizable to PTP or nPTP genes or transripts, or antibodies specific for, nPTP, PTP, or their functional derivatives.

By "human subject" is meant any human being or any developmental form thereof, such as a human embryo or fetus, prior to birth.

Antibodies directed against PTP can be used, as taught by the present invention, to detect and diagnose neurological or pancreatic disease (such as acute or chronic pancreatitis, where levels can exceed 150 ng/ml in biological fluids).

The diagnostic methods of the present invention do not require invasive removal of neural tissue. Diseases such as AD and DS, neural tube defects such as anencephaly, spina bifida, meningocele, meningomyelocele, holoprosencephaly, and the like, may be diagnosed using the methods of the present invention. In addition, pancreatic disease, such as acute and chronic pancreatitis, may be diagnosed using the methods of the present invention.

The present invention additionally pertains to assays, both nucleic acid hybridization assays (described above) and immunoassays, for detecting the presence of PTP or nPTP in cells or in the biological fluids of a human subject using light or electron microscopic histology, imaging, radioactive or enzyme based assays, and the like.

Various histological staining methods, including immunohistochemical staining methods, may also be used effectively according to the teaching of the invention. Silver stain is but one method of visualizing PTP. Other staining methods useful in the present invention will be obvious to the artisan, the determination of which would not involve undue experimentation (see generally, for example, A *Textbook of Histology*, Eds. Bloom and Fawcett, W. B. Saunders Co., Philadelphia (1964)).

One screening method for determining whether a given compound is a PTP or nPTP functional derivative comprises, for example, immunoassays employing RIA or ELISA methodologies, based on the production of specific antibodies (monoclonal or polyclonal) to PTP or nPTP. Other suitable screening methods will be readily apparent to those of skill in the art.

As is also apparent, the detection or diagnosis of AD, DS, neural tube defects, or pancreatic disease may be augmented through the use of PTP or nPTP mutants or variants possessing additional amino acid residues added to enhance its coupling to a carrier or to enhance the activity of PTP or nPTP. The scope of the present invention is further intended to include mutant forms of PTP or nPTP (including PTP or nPTP molecules which lack certain amino acid residues).

The present invention also relates to methods of detecting PTP, nPTP, or their functional derivatives in a sample or subject. For example, antibodies specific for PTP, nPTP, or their functional derivatives, may be detectably labeled with any appropriate marker, for example, a radioisotope, an enzyme, a fluorescent label, a paramagnetic label, or a free radical. Methods of making and detecting such detectably labeled antibodies or their functional derivatives are well known to those of ordinary skill in the art, and are described in more detail below. Standard reference works setting forth the general principles of immunology include the work of Klein, J. (*Immunology: The Science of Self-Nonself Discrimination*, John Wiley & Sons, New York (1982)); Kennett, R., et al. (*Monoclonal Antibodies and Hybridomas: A New Dimension in Biological Analyses*, Plenum Press, New York (1980)); Campbell, A. ("Monoclonal Antibody Technology," In: *Laboratory Techniques in Biochemistry and Molecular Biology*, Volume 13 (Burdon, R., et al., eds.), Elsevier, Amsterdam (1984)); and Eisen, H. N., (In: *Microbiology*, 3rd Ed. (Davis, B. D., et al., Harper & Row, Philadelphia (1980)).

The term "antibody" refers both to monoclonal antibodies which are a substantially homogeneous population and to polyclonal antibodies which are heterogeneous populations. Polyclonal antibodies are derived from the sera of animals immunized with an antigen. Monoclonal antibodies (mAbs) to specific antigens may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, IgD and any subclass thereof. The monoclonal antibodies, particularly mAbs 7, 9, and 10, used in the present invention, may be prepared as previously described (Gross et al., *J. Clin. Invest.* 76:2115–2126 (1985); see Example II).

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of PTP or nPTP according to the methods disclosed herein in order to detect and diagnose AD, DS, neural tube defects, or pancreatic disease in the same manner as an intact antibody. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopic determinants usually consist of chemically active surface groupings of molecules such as amino acids or sugar side chains and have specific three dimensional structural characteristics as well as specific charge characteristics.

An "antigen" is a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence of cells which contain the PTP or nPTP antigens. Thus, the antibodies (of fragments thereof) useful in the present invention may be employed histologically to detect or visualize the presence of PTP or nPTP. Thus, the presence of nPTP above approximately 20 ng/ml concentration, as previously described, may be used as a diagnostic test for AD and DS. The presence of nPTP above approximately 200 ng/ml may be used as a diagnostic test for neural tube defects. The presence of PTP above approximately 150 ng/ml concentration may be used as a diagnostic test for pancreatic disease. Such an assay for PTP or nPTP typically comprises incubating a biological sample from said subject suspected of having such a condition in the presence of a detectably labeled binding molecule (e.g., antibody) capable of identifying PTP or nPTP, and detecting said binding molecule which is bound in a sample.

Thus, in this aspect of the invention, a biological sample may be treated with nitrocellulose, or other solid support which is capable of immobilizing cells, cell particles or soluble proteins. The support may then be washed with suitable buffers followed by treatment with the detectably labeled nPTP-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will note many other suitable carriers for binding monoclonal antibody or antigen, or will be able to ascertain the same by use of routine experimentation.

It should be apparent that all of the methods described herein apply equally to assays utilizing the native PTP antigen, as well as the nPTP antigen. Thus, PTP may be substituted for nPTP in the description of the following assays.

One embodiment for carrying out the diagnostic assay of the present invention on a biological sample containing nPTP, comprises:

(a) contacting a detectably labeled nPTP-specific antibody with a solid support to effect immobilization of said nPTP-specific antibody or a fragment thereof;

(b) contacting a sample suspected of containing nPTP with said solid support;

(c) incubating said detectably labeled nPTP-specific antibody with said support for a time sufficient to allow the immobilized nPTP-specific antibody to bind to the nPTP;

(d) separating the solid phase support from the incubation mixture obtained in step (c); and (e) detecting the bound label and thereby detecting and quantifying nPTP.

Alternatively, labeled nPTP-specific antibody/nPTP complexes in a sample may be separated from a reaction mixture by contacting the complex with an immobilized antibody or protein which is specific for an immunoglobulin, e.g., Staphylococcus protein A, Staphylococcus protein G, anti-IgM or anti-IgG antibodies. Such anti-immunoglobulin antibodies may be polyclonal, but are preferably monoclonal. The solid support may then be washed with a suitable buffer to give an immobilized nPTP/labeled nPTP-specific antibody complex. The label may then be detected to give a measure of nPTP.

This aspect of the invention relates to a method for detecting nPTP or a fragment thereof in a sample comprising:

(a) contacting a sample suspected of containing nPTP with an nPTP-specific antibody or fragment thereof which binds to nPTP; and (b) detecting whether a complex is formed.

The invention also relates to a method of detecting nPTP in a sample, further comprising:

(c) contacting the mixture obtained in step (a) with an Fc binding molecule, such as an antibody, Staphylococcus protein A, or Staphylococcus protein G, which is immobilized on a solid phase support and is specific for the nPTP-specific antibody to give a nPTP/nPTP-specific antibody immobilized antibody complex;

(d) washing the solid phase support obtained in step (c) to remove unbound nPTP/nPTP-specific antibody complex; and (e) detecting the label bound to said solid support.

Of course, the specific concentrations of detectably labeled antibody and nPTP, the temperature and time of incubation, as well as other assay conditions may be varied, depending on various factors including the concentration of nPTP in the sample, the nature of the sample, and the like. The binding activity of a given lot of anti-PTP antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the nPTP-specific antibody can be detectably labeled is by linking the same to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the nPTP-specific antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection may be accomplished using any of a variety of immunoassays. For example, by radioactively labeling the nPTP-specific antibodies or antibody fragments, it is possible to detect nPTP through the use of radioimmune assays.

A good description of a radioimmune assay (RIA) may be found in *Laboratory Techniques and Biochemistry in Molecular Biology*, by Work, T. S., et al., North Holland Publishing Company, NY (1978), with particular reference to the chapter entitled "An Introduction to Radioimmune Assay and Related Techniques" by Chard, T., incorporated by reference herein.

The radioactive isotope can be detected by such means as the use of a gamma counter or a scintillation counter or by audioradiography. Isotopes which are particularly useful for the purpose of the present invention are: $^3H$, $^{125}I$, $^{131}I$, $^{35}S$, $^{14}C$, and preferably $^{125}I$ (see Example IV).

It is also possible to label the nPTP-specific antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerytherin, phycocyanin, allophycocyanin, o-phthaldehyde and fluorescamine.

The nPTP-specific antibody can also be detectably labeled using fluorescence emitting metals such as $^{152}Eu$, or others of the lanthanide series. These metals can be attached to the nPTP-specific antibody using such metal chelating groups as diethylenetriaminepentaacetic acid (DTPA) or ethylenediaminetetraacetic acid (EDTA).

The nPTP-specific antibody also can be detectably labeled by coupling it to a chemiluminescent compound. The presence of the chemiluminescent-tagged nPTP-specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the nPTP-specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the nPTP-specific antibody may be accomplished by a scintillation counter, for example, if the detectable label is a radioactive gamma emitter, or by a fluorometer, for example, if the label is a fluorescent material. In the case of an enzyme label, the detection can be accomplished by calorimetric methods which employ a substrate for the enzyme. Detection may also be accomplished by visual comparison of the extent of enzymatic reaction of a substrate in comparison with similarly prepared standards.

The detection of foci of such detectably labeled antibodies is indicative of a disease or dysfunctional state as previously described. For the purposes of the present invention, the nPTP which is detected by this assay may be present in a biological sample. Any sample containing nPTP can be used. However, one of the benefits of the present diagnostic invention is that invasive tissue removal may be avoided. Therefore, preferably, the sample is a biological solution such as, for example, cerebrospinal fluid, amniotic fluid, blood, serum, urine and the like. However, the invention is not limited to assays using only these samples, it being possible for one of ordinary skill in the art to determine suitable conditions which allow the use of other samples.

For example, the three-site M-IRMA may be used to measure nPTP levels in a biological fluid, such as CSF. It is possible to obtain, by spinal tap, on a routine basis, CSF from individuals suspected of having AD. The M-IRMA described by the present invention accurately measures nPTP levels in CSF. Thus, the diagnosis of AD can be established by a simple, non-invasive immunoassay which discloses nPTP levels greatly increased over normal levels (see FIG. 7).

In one embodiment, as described above, this examination for neurological or pancreatic disease or dysfunction is accomplished by removing samples of biological fluid and incubating such samples in the presence of detectably labeled antibodies (or antibody fragments). In a preferred embodiment, this technique is accomplished in a noninvasive manner through the use of magnetic imaging, fluorography, etc.

Preferably, the detection of cells which express nPTP may be accomplished by in vivo imaging techniques, in which the labeled antibodies (or fragments thereof) are provided to a subject, and the presence of the nPTP is detected without the prior removal of any tissue sample. Such in vivo detection procedures have the advantage of being less invasive than other detection methods, and are, moreover, capable of detecting the presence of nPTP in tissue which cannot be easily removed from the patient, such as brain tissue.

There are many different in vivo labels and methods of labeling known to those of ordinary skill in the art. Examples of the types of labels which can be used in the present invention include radioactive isotopes and paramagnetic isotopes. Those of ordinary skill in the art will know of other suitable labels for binding to the antibodies used in the invention, or will be able to ascertain such, using routine experimentation. Furthermore, the binding of these labels to the antibodies can be done using standard techniques common to those of ordinary skill in the art.

For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention.

Another important factor is selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in the 140–200 keV range, which maybe readily detected by conventional gamma cameras.

For in vivo diagnosis radionuclides may be bound to antibody either directly or indirectly by using an intermediary functional group. Intermediary functional groups which are often used in binding radioisotopes which exist as metallic ions to immunoglobulins are DTPA and EDTA. Typical examples of ions which can be bound to immunoglobulins are $^{99m}$Tc, $^{123}$I, $^{111}$In, $^{131}$I, $^{97}$Ru, $^{67}$Cu, $^{67}$Ga, $^{125}$I, $^{68}$Ga, $^{72}$As, $^{89}$Zr, and $^{201}$Tl.

The antibodies useful in the invention can also be labeled with paramagnetic isotopes for purposes of in vivo diagnosis. Elements which are particularly useful, as in Magnetic Resonance Imaging (MRI), include $^{157}$Gd, $^{55}$Mn, $^{162}$Dy, and $^{56}$Fe.

The antibodies (or fragments thereof) useful in the present invention are also particularly suited for use in in vitro immunoassays to detect the presence of nPTP in body tissue, fluids (such as CSF, amniotic fluid, blood, lymph, etc.), or cellular extracts. In such immunoassays, the antibodies (or antibody fragments) may be utilized in liquid phase or, preferably, bound to a solid-phase carrier, as described above.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. (*Clin. Chim. Acta* 70:1–31 (1976)), and Schurs, A. H. W. M., et al. (*Clin. Chim. Acta* 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

In situ detection may be accomplished by removing a histological specimen from a patient, and providing the combination of labeled antibodies of the present invention to such a specimen. The antibody (or fragment) is preferably provided by applying or by overlaying the labeled antibody (or fragment) to a biological sample. Through the use of such a procedure, it is possible to determine not only the presence of nPTP, but also the distribution of nPTP on the examined tissue. Using the present invention, those of ordinary skill will readily perceive that any of a wide variety of histological methods (such as staining procedures) can be modified in order to achieve such in situ detection.

The binding molecules of the present invention may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., CSF, amniotic fluid, blood, lymph, tissue homogenate, etc.) and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. Such "two-site" or "sandwich" assays are described by Wide at pages 199–206 of Radioimmune Assay Method, edited by Kirkham and Hunter, E. & S. Livingstone, Edinburgh, 1970.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

In a preferred embodiment, a combination of the monoclonal antibodies of the present invention may be used to construct a sensitive three-site monoclonal immunoradiometric assay. mAbs 7 and 10 may be used as capture antibodies on a solid phase support and $^{125}$I-9 mAb may be used as a tracer. Other combinations of these antibodies may also be used, as shown in Table I.

TABLE I

| mAb on Solid-Phase Support | $^{125}$I mAb (Probe) | Format | CPM Bound (Neg. Controls) | CPM Bound (10 ng/ml PTP) |
|---|---|---|---|---|
| 7 | 9 | One step* | 190 ± 10 | 1,765 ± 10 |
| 10 | 9 | One step | 275 ± 25 | 2,900 ± 45 |
| 7 + 10 | 9 | One step | 360 ± 20 | 3,610 ± 55 |
| 7 + 10 | 9 | Two steps** | 70 ± 12 | 5,500 ± 150 |

*Simultaneous sandwich assay.
**Forward sandwich assay and preferred assay design for measurement of nPTP.

The above-described in vitro or in vivo detection methods may be used in the detection and diagnosis of AD, DS, neural tube defects, or pancreatic disease without the necessity of removing tissue. Such detection methods may be used to assist in the determination of the stage of neurological deterioration in AD by evaluating and comparing the concentration of nPTP in the biological sample. A concentration above approximately 20 ng/ml of nPTP would be diagnostic of AD.

In addition, these antibodies can be used in the above-described combinations to diagnose chronic or acute pancreatic disease by assaying biological samples such as blood, urine, serum, and the like, and detecting the presence of PTP in said sample.

In acute and chronic pancreatic disease, blood or serum levels of PTP above approximately 150 ng/ml indicate damage to the pancreatic acinar cells, regardless of etiology. Since PTP has a low molecular weight and will pass through the glomerulus (exclusion size >50,000 daltons), urine PTP levels also indicate the presence of acute and chronic pancreatic damage due to alcohol, trauma, gallstone, penetrating peptic ulcer, etc. Levels of PTP as measured by the three-site M-IRMA in urine of above approximately 500 ng/ml also indicate injury to the pancreas.

Additionally, these methods may be employed in determining whether a subject suffers from DS or neural tube defects, particularly prenatally. A concentration above approximately 20 ng/ml of nPTP in a biological sample would be diagnostic of DS. A high concentration of nPTP (i.e., above approximately 200 ng/ml), or different molecular forms of nPTP (see FIG. 8) in a biological sample would indicate the existence of a congenital malformation such as a neural tube defect in a subject.

As used herein, an effective amount of a diagnostic reagent (such as an antibody or antibody fragment) is one capable of achieving the desired diagnostic discrimination and will vary depending on such factors as age, condition, sex, the extent of disease of the subject, counterindications, if any, and other variables to be adjusted by the physician. The amount of such materials which are typically used in a diagnostic test are generally between 0.1 to 5 mg, and preferably between 0.1 to 0.5 mg.

The assay of the present invention is also ideally suited for the preparation of a kit. Such a kit may comprise a carrier means being compartmentalized to receive in close confinement therewith one or more container means such as vials, tubes and the like, each of said container means comprising the separate elements of the immunoassay.

For example, there may be a container means containing the first antibody immobilized on a solid phase support, and a further container means containing detectably labeled titrating antibodies in solution. Further container means may contain standard solutions comprising serial dilutions of PTP or nPTP to be detected. The standard solutions of PTP or nPTP may be used to prepare a standard curve with the concentration of PTP or nPTP plotted on the abscissa and the detection signal on the ordinate. The results obtained from a sample containing PTP or nPTP may be interpolated from such a plot to give the concentration of PTP or nPTP.

EXAMPLES

EXAMPLE I

Immunohistochemical Studies of nPTP in Patient Tissues

A. Tissue Preparation

Brain tissue from patients with AD, Down syndrome, neurologically intact controls, and demented controls without AD was obtained at post-mortem examination, and harvested within 12 hours of death. The brains were cut immediately, and tissue blocks not larger than 2×2×1 cm from defined regions were snap frozen in isopentane cooled with dry ice and then stored at −80° C. for future biochemical and immunohistochemical studies. Adjacent identical tissue blocks were fixed in neutral buffered 10% formaldehyde solution, embedded in paraffin and subsequently processed for histopathological diagnosis and immunocytochemistry.

B. Histopathologic Diagnosis

Adjacent 8–10 $\mu$m-thick paraffin tissue sections were dewaxed and stained with Luxol fast blue-hematoxylin-eosin, Bodian silver impregnation, Bielschowski's silver impregnation, and congo red. The diagnosis of AD was established by ascertaining the presence of abundant neuritic plaques, neurons with NFTs and granulovacuolar degeneration, and amyloid deposition both within plaques and walls of cerebral blood vessels. Tissue sections from control brains were similarly processed to establish the correct diagnosis or confirm the absence of lesions, as well as exclude the diagnosis of AD.

C. Immunohistochemistry

Cryostat and de-waxed, re-hydrated paraffin sections 12 $\mu$m thick were equilibrated in phosphate buffered saline (PBS: 10 mM phosphate, 0.9% NaCl, pH 7.30) and then pre-incubated in normal goat serum for 30 minutes to block non-specific absorption of antibody. The sections were incubated with mouse monoclonal antibody to the 9 epitope of nPTP or neurofilament antigen (cocktail of polyclonal antibodies against all three molecular weight forms) for 1 hour. Endogenous peroxidase activity was abolished by treating the sections with 0.03% $H_2O_2$ in PBS for 30 minutes. Immunoreactive cells were detected using the avidinbiotinhorseradish peroxidase complex method (ABC: Vector Laboratory) with 3—3'-diaminobenzidine (DAB) as the chromogen according to the manufacturer's instructions. Enhancement of the reaction product was achieved by co-precipitating the DAB with cobalt chloride (0.08%). The immunoreactive tissue sections were dehydrated in graded alcohols, cleared in xylenes, and cover-slipped with Permount adhesive. The sections were examined by light microscopy and the number of immunolabeled cells in 20 adjacent 250× fields was determined.

EXAMPLE II

Preparation of Monoclonal Antibodies

The preparation of monoclonal antibodies (mAbs) to human PTP has been previously described (Gross et al., *J. Clin. Invest.* 76:2115–2126 (1985)). Monoclonal antibodies referred to as 7, 9 and 10 in this application have been shown to recognize distinct and separate epitopes on PTP (Gross et al., ibid) as well as nPTP. Ascites fluids were prepared by injection of hybridoma cells intraperitoneally (i.p.) into Balb/c mice primed with 2, 6, 10, 14-tetramethylpentadecane. mAbs were subsequently purified by Protein A-conjugated Sepharose 4B columns and labeled with $^{125}$I as previously reported (Wilson et al., *Proc. Natl. Acad. Sci. USA* 85:3140–3144 (1988)).

EXAMPLE III

Preparation of Brain Extracts

Brain tissue was weighed and homogenized with a polytron homogenizer in five volumes of 10 mM Phosphate buffer (pH 7.2) containing 150 mM NaCl and 0.1% NaN$_3$ (PBS). Extracts were centrifuged at 10,000 g for 15 minutes at 4° C. The supernatant was used for the measurement of nPTP immunoreactivity and protein content (Lowry et al., *J. Biol. Chem.* 193:265–275 (1951)). The pellet was resuspended in PBS and used for the determination of DNA content as previously described (Becker et al., *Analytical Biochemistry* 127:302–307 (1982)).

EXAMPLE IV

Immunochemical Mapping of PTP in Neural Tissue

Purified human PTP suspended in PBS at neutral pH was diluted from 1 to 100 ng/ml in calf serum to prepare standards. Epitope mapping studies were performed by comparing the profiles of the PTP pancreatic standard to that found in AD brain. The detection by anti-PTP mAbs of epitopes on nPTP in AD brain tissue extracts was performed as follows: Polystyrene beads (Precision Plastic Ball, No. Chicago, Ill.) were coated with one of the three anti-PTP mAbs (ascites fluid diluted 1:500 in PBS) by overnight incubation at 20° C. Beads were washed with distilled water before use. 200 µl of tissue extract or PTP standard and the antibody-coated beads were then incubated overnight to capture any antigen presenting the epitope of interest. The beads were then washed with distilled water to eliminate nonbound material. Antigen captured by the mAb-coated beads was then detected by incubation with one of the $^{125}$I-labeled anti-PTP mAbs (200 µl containing 100,000 cpm in 20% cell serum in PBS). After a 4 hr incubation at 20° C., beads were washed and bound radioactivity determined by a gamma well counter.

EXAMPLE V

Monoclonal Immunoradiometric Assay (M-IRMA)

Three mAbs directed against different epitopes on human PTP were used to construct a sensitive three-site IRMA. mAbs 7 and 10 were used as capture antibodies on the solid phase support and $^{125}$I-9 mAb was used as the tracer. 200 µl of tissue extract or PTP standard was incubated with the mAb-coated polystyrene beads overnight at 20° C. After extensive washing of unbound material, the beads were incubated with 200 µl (100,000 cpm) of $^{125}$I-9. The tracer antibody solution contained 20% calf serum (CS) and 20 µg/100 µl of a nonspecific mouse mAb blocking antibody. After a 4 hr incubation at 20° C., beads were washed again and counted as described above. For standards, purified PTP diluted in 20% CS or 10% Bovine Serum Albumin-PBS (BSA-PBS) was used. Brain tissue homogenates and normal pancreatic fluid were assayed either directly or after dilution in CS or BSA-PBS. Determination of nPTP concentrations was determined from the standard curve (linear from 1–10 ng/ml). The lower limit of sensitivity was found to be 50 pg/ml serum.

EXAMPLE VI

Polyacrylamide Gel Electrophoresis

Purified PTP, normal pancreatic fluid and saline extracts prepared from AD brain were analyzed on 15% polyacrylamide gels in the presence of sodium dodecyl sulfate (SDS-PAGE). Samples containing 100–500 µg protein were first diluted in SDS-sample buffer without reducing agents. Following electrophoresis, the wet gels were cut into 2 mm fractions using a gel slicer. Proteins were eluted from the gel fractions by shaking 24–72 hours at 4° C. with 1 ml PBS containing 1% BSA and 0.2% NaN$_3$. The eluates were analyzed for nPTP activity by M-IRMA. Prestained protein molecular weight markers (Bio-Rad: Richmond, Calif.) co-migrated with the analyzed samples and were used to estimate the apparent molecular weight of the material with nPTP-immunoreactivity.

EXAMPLE VII

Measurement of nPTP Immunoreactivity nPTP concentrations were measured by the 3 site M-IRMA in various regions of an AD brain including areas 11 and 8/9 of the frontal cortex, 20/21 of the temporal association cortex, 17 of the visual association cortex, 40 and 45 of the parietal cortex, and cerebellum (CB), and these results were compared to similar areas from a normal brain. As shown in FIG. 1, nPTP levels were strikingly elevated in all areas of AD brain tested and were 50 to 100 times the levels found in the corresponding areas of a normal brain. Results were unaffected by the method of measurement with the notable exception of CB where nPTP levels were lower than other areas when expressed as ng/mg DNA.

EXAMPLE VIII

Epitope Mapping of nPTP in AD Brain

Figure 2B:
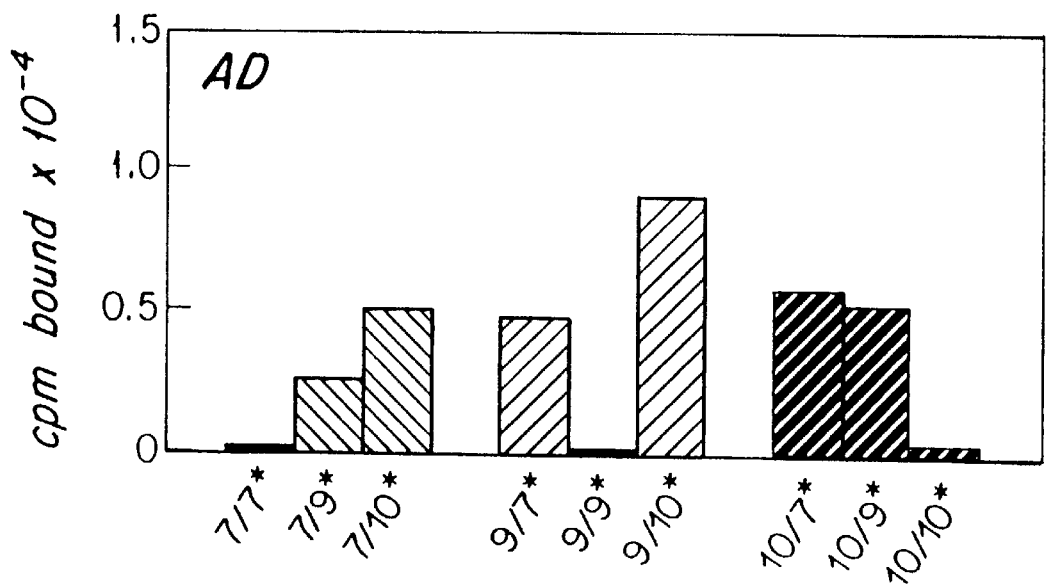

In order to determine if all three epitopes found on the pancreatic form of PTP were present in AD brain, the inventors employed the mAbs in combination, in the construction of 9 different IRMAs. FIG. 2 depicts these results, designed to measure separate and distinct epitopes on the nPTP molecule. The binding profiles of PTP in pancreatic juice and nPTP immunoreactivity in AD brain are similar. It is noteworthy that these three epitopes are not repeating since the homologous IRMAs of 7/7*, 9/9* and 10/10* (indicating that the capture and detecting antibody are the same) gave no or very low binding activity. Thus, the epitopes detected by the mAbs in the native pancreatic PTP and the nPTP found in AD brain are the same.

EXAMPLE IX

Quantitative Analysis of Soluble nPTP Immunoreactivity in Brain Tissue

Figure 3:
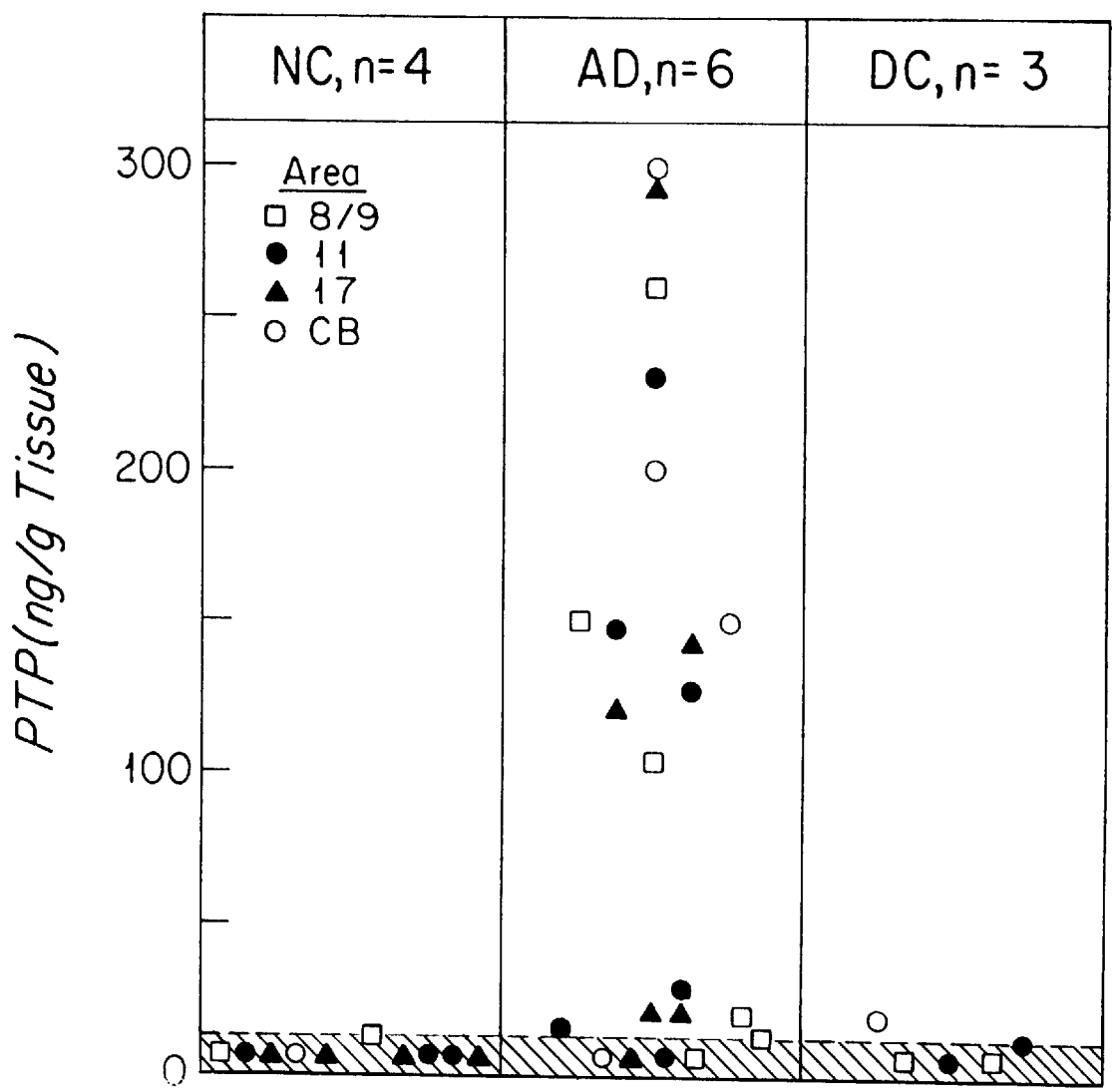
FIG. 3. Quantitative soluble nPTP levels measured by a three site M-IRMA in various brain regions of normal controls (NC), AD patients and disease controls (DC). The shaded area represents the range of nPTP values found in NC and DC brains. One AD brain had normal levels of nPTP in regions CB, 11, 17 and 8/9. However, the histopathologic changes of AD in this brain were only observed in the hippocampus.
Figure 4A:
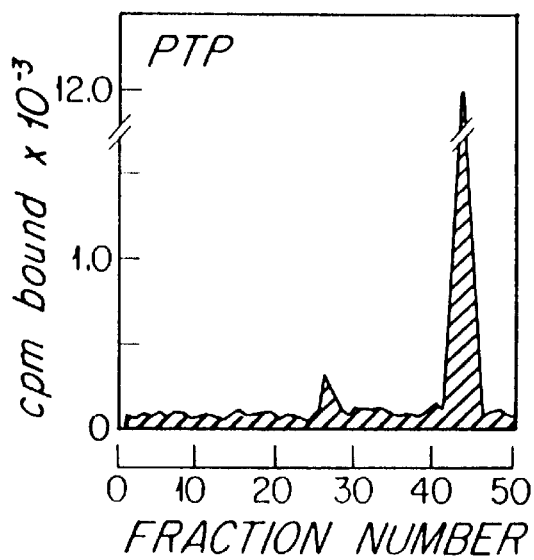
FIG. 4. Molecular size of central nervous system nPTP in 4 AD brains compared to purified nPTP standard and PTP in pancreatic fluid (PF). The apparent molecular weight of the taller nPTP peak is 14.4 kD and the shorter peak is approximately 26 kD (hatched areas). AD brain nPTP immunoreactivity had a range between 17 and 20 kD and all 4 subjects have the same species.
Figure 4B:
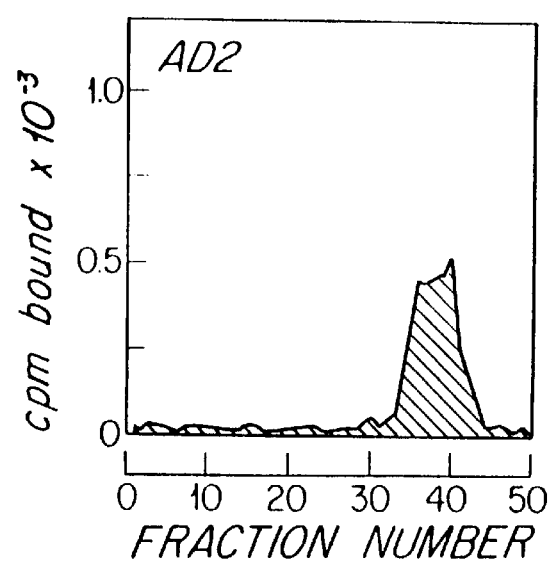
Figure 4C:
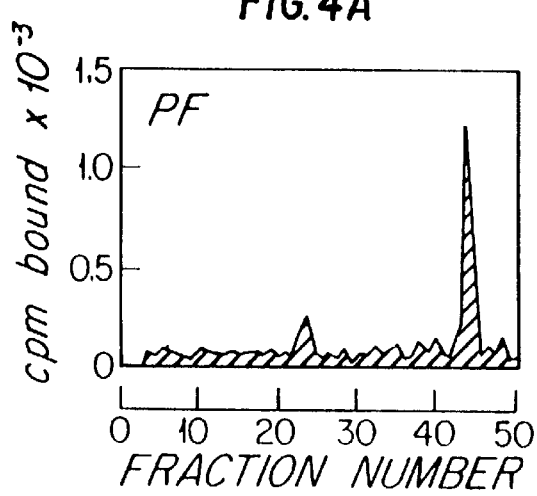
Figure 4D:
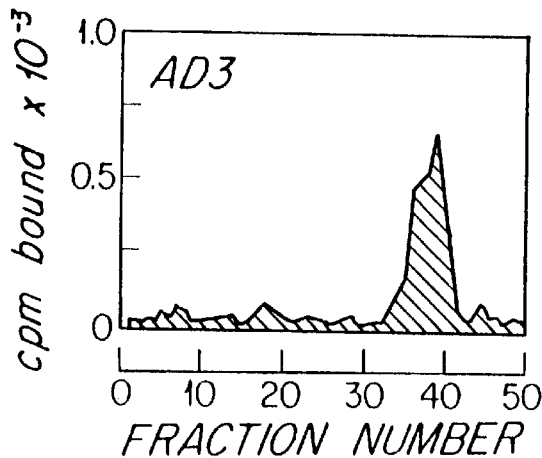
Figure 4E:
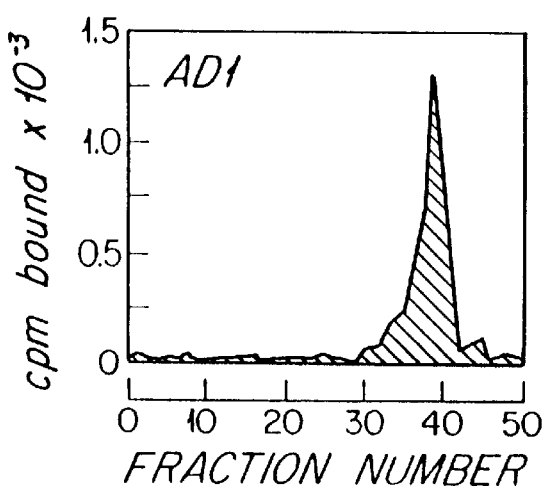
Figure 4F:
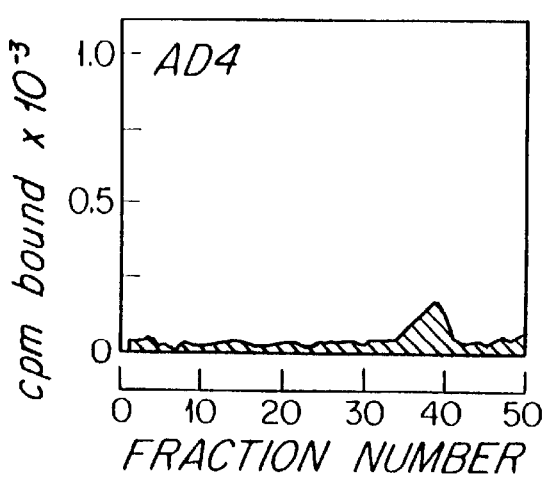
Figure 5A:
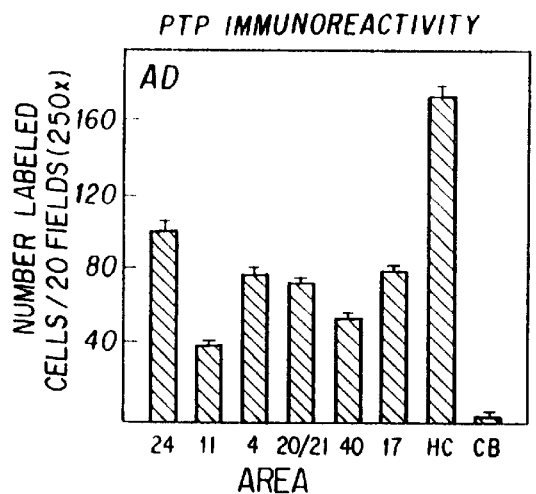
FIG. 5. Distribution and number of neurons bearing neurofibrillary tangles (NFT) and nPTP immunoreactivity in AD, DS, and normal brains. Various brain regions were analyzed and the results expressed as the number of positive staining cells per 20 fields at 250X. HC=hippocampus, CB=cerebellum.
Figure 5B:
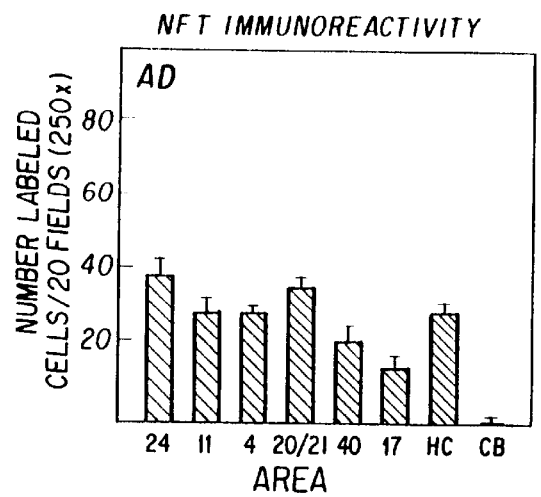
Figure 5C:
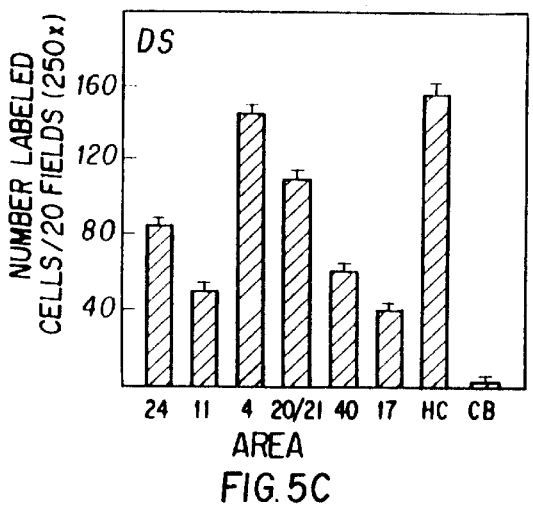
Figure 5D:
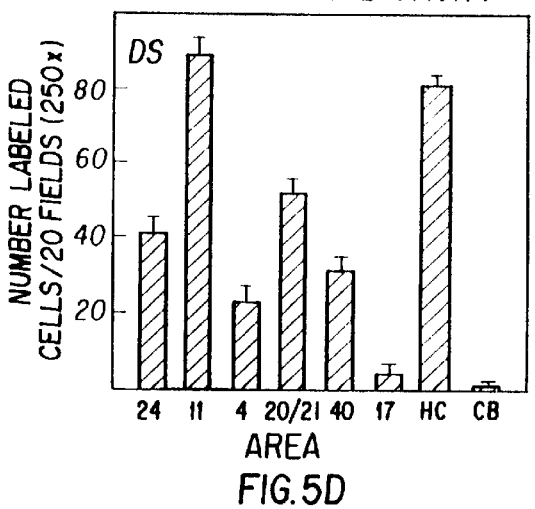
Figure 5E:
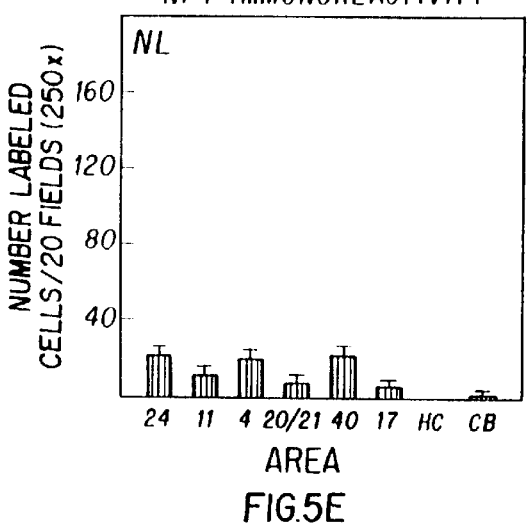
Figure 5F:
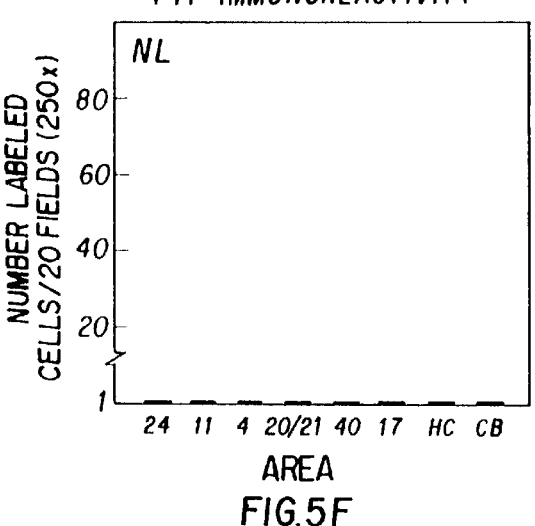
Figure 6A:
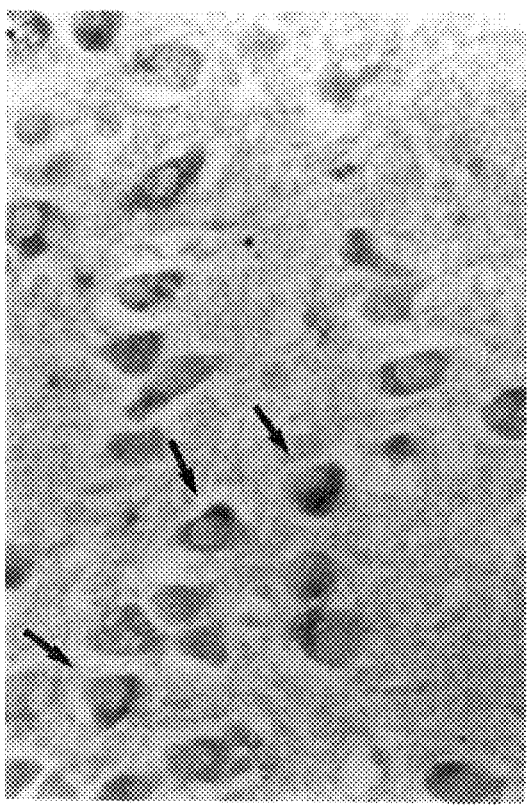
FIG. 6. Immunoperoxidase staining of frontal cortex derived from AD and normal brain. The top panel represents cells from AD brain stained with: mAb 9 for the presence of nPTP (A) and NFTs (B) with a polyclonal antiserum. The bottom panel represents PTP (C) and NFTs (D) immunoreactivity of normal brain. The arrows indicate positive staining cells. The large neurons that stained positive for NFTs were also highly immunoreactive for nPTP (compare A and B). Comparable regions of control brain had no such immunoreactivity.
Figure 6B:
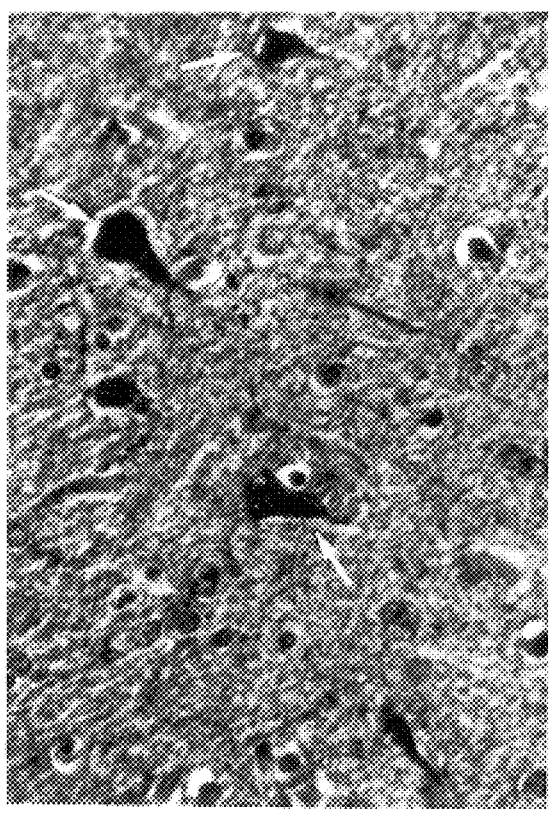
Figure 6C:
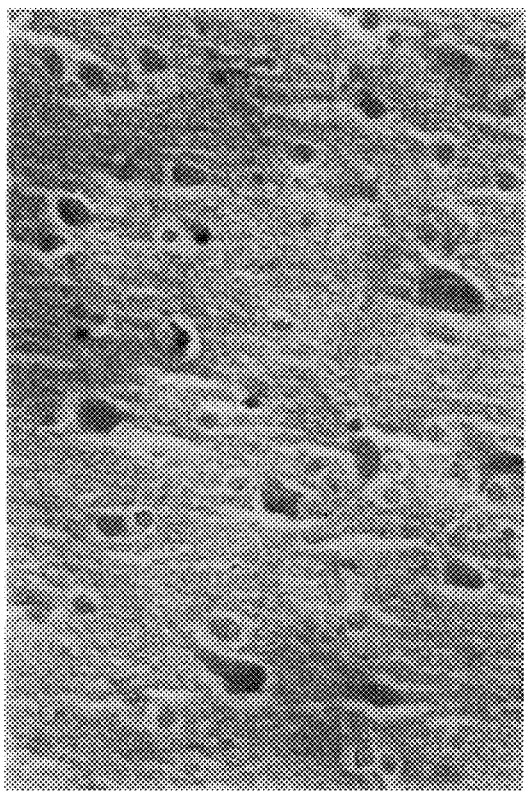
Figure 6D:
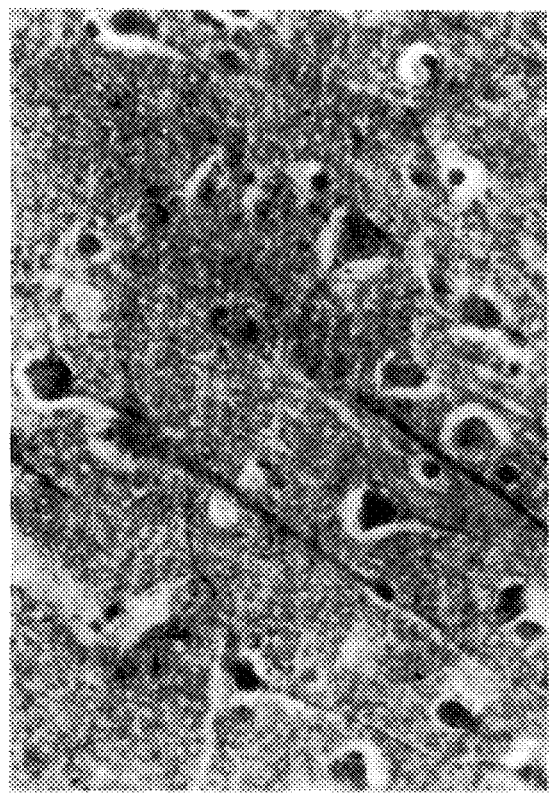

Soluble extracts from 71 brain tissue samples derived from 6 subjects with AD, 3 normal controls and 3 other disease controls (Schizophrenia, Multi-infarct Dementia and Parkinson's Disease) were analyzed. Brain areas 6, 8/9, 11, 17, 20/21, 40, 45 and CB were analyzed from the same subject in most cases. Areas 2 and 4 were studied in a few cases. FIG. 3 illustrates the results of these measurements.

Normal controls had low but detectable levels of nPTP immunoreactivity in various regions of the brain. Concentrations ranged from 1 to 11 ng/gm tissue wet weight with a mean value for normal brain of 5 ng/gm tissue. In contrast, 5 of 6 AD patients were found to have nPTP levels above the normal range. Levels varied from 12 to 295 ng/gm with a mean of 116 ng/gm. In general, there appeared to be few variations in nPTP concentrations between several areas of brain derived from the same patient (see FIG. 1). It is noteworthy that the other and only case of AD where nPTP levels were found to be within the normal range in areas 6, 8/9, 11, 20/21, 45 and CB revealed no pathologic changes characteristic of the disease. In this individual, neuritic plaques and NFTs were found only in the hippocampus; nPTP immunoreactivity however was demonstrated in the involved neurons in this case by histochemical staining as described below. Finally, measured nPTP immunoreactivity in Schizophrenia, Parkinson's Disease and Multi-Infarct Dementia brain was similar to that found in normal controls (FIG. 3).

EXAMPLE X

Molecular Forms of nPTP in AD Brains

The molecular weight of the material with binding activity in AD brain (nPTP) was compared to pancreatic fluid PTP, as shown in FIG. 4. All 4 AD brains studied had the same species of nPTP that migrated slightly slower than the major peak of the native form of PTP (M.W. approximately 14 kd). The range of nPTP immunoreactivity varied between 17 and 20 kd. Thus, the soluble nPTP found in AD brain has a definable molecular form similar to, but higher than, that found in pancreatic fluid.

EXAMPLE XI

Immunohistochemical Staining and Cellular Location

Immunohistochemical staining with anti-neurofilament antibody demonstated abundant NFTs in brains from subjects with AD and DS, as shown in FIG. 5. Although there was variability in the density of NFTs among the subjects, in AD the high densities were present in the front cortex, including Areas 24, 11 and 4, the temporal association cortex (Area 20/21) and the hippocampal formation. Lower but moderate densities of NFTs were observed in the parietal cortex (Area 40) and primary and association visual cortex (Areas 17 and 18). NFTs were either rare or absent in the cerebellum.

In DS, NFTs were distributed a manner similar to AD, but their densities were strikingly greater in Area 11, Area 20/21 and the hippocampus, an already recognized histopathological distinction between AD and DS. In addition, NFTs occurred infrequently in both Areas 17 and 18, and in the cerebellum. Control brains had only rare, scattered NFTs.

Cells immunolabeled with anti-PTP antibody were observed in brains from patients with AD and DS, which also contained no neuropathology. The density of immunolabeled cells and the intensity of immunolabeling were considerably less in control brains compared with either AD or DS brain (FIG. 5).

In AD, the highest densities of nPTP-containing cells were located in Area 24 and the hippocampal formation. All of the other regions manifested similar densities of nPTP-containing cells, except for the cerebellum, which was devoid of such cells. Large pyramidal neurons were most conspicuously labeled, and surprisingly, those cells also appeared to contain either NFTs or represent the population of neurons which characteristically develop NFTs in AD, as illustrated in FIG. 6. In addition, rare neuritic plaques were visualized with the anti-PTP antibody. To quite a varied extent, reactive fibrous astrocytes were immunoreactive for nPTP, but in contrast to neurons in which the immunolabeling was smooth and fibrillary, the immunoreactivity in astrocytes appeared beaded and granular.

The granular character of nPTP immunoreactivity within astrocytes may indicate a different form of the molecule compared with what exists within neurons. It may represent a phagocytized, partially digested product, or it may be a site of nPTP synthesis.

Finally, the neuropil throughout all regions of cerebral cortex contained extremely fine, thread-like fibrils immunoreactive for nPTP. There did not appear to be an association between nPTP immunoreactivity and blood vessels or white matter, and small neurons usually lacked nPTP immunoreactivity.

In DS, the pattern of immunolabeling and density of nPTP-containing neurons were similar to those observed in AD. The only notable differences were the higher densities of immunolabeled neurons in Areas 4 and 20/21 and lower density of nPTP-containing neurons in Areas 17/18 of DS brain. To some extent this result parallels the differences in densities of NFTs observed between AD and DS.

In control brains the density of nPTP-containing neurons was strikingly lower than in either AD or DS and the intensity of immunolabeling was comparatively weak. In addition, the thread-like labeling of the neuropil was essentially absent in control brains.

EXAMPLE XII

Elevated Levels of nPTP in CSF Derived from AD-afflicted Subjects

The inventors studied 12 subjects with AD and two normal subjects. CSF was obtained at the time of autopsy so that the diagnosis of AD was established by histopathologic criteria.

Figure 7:
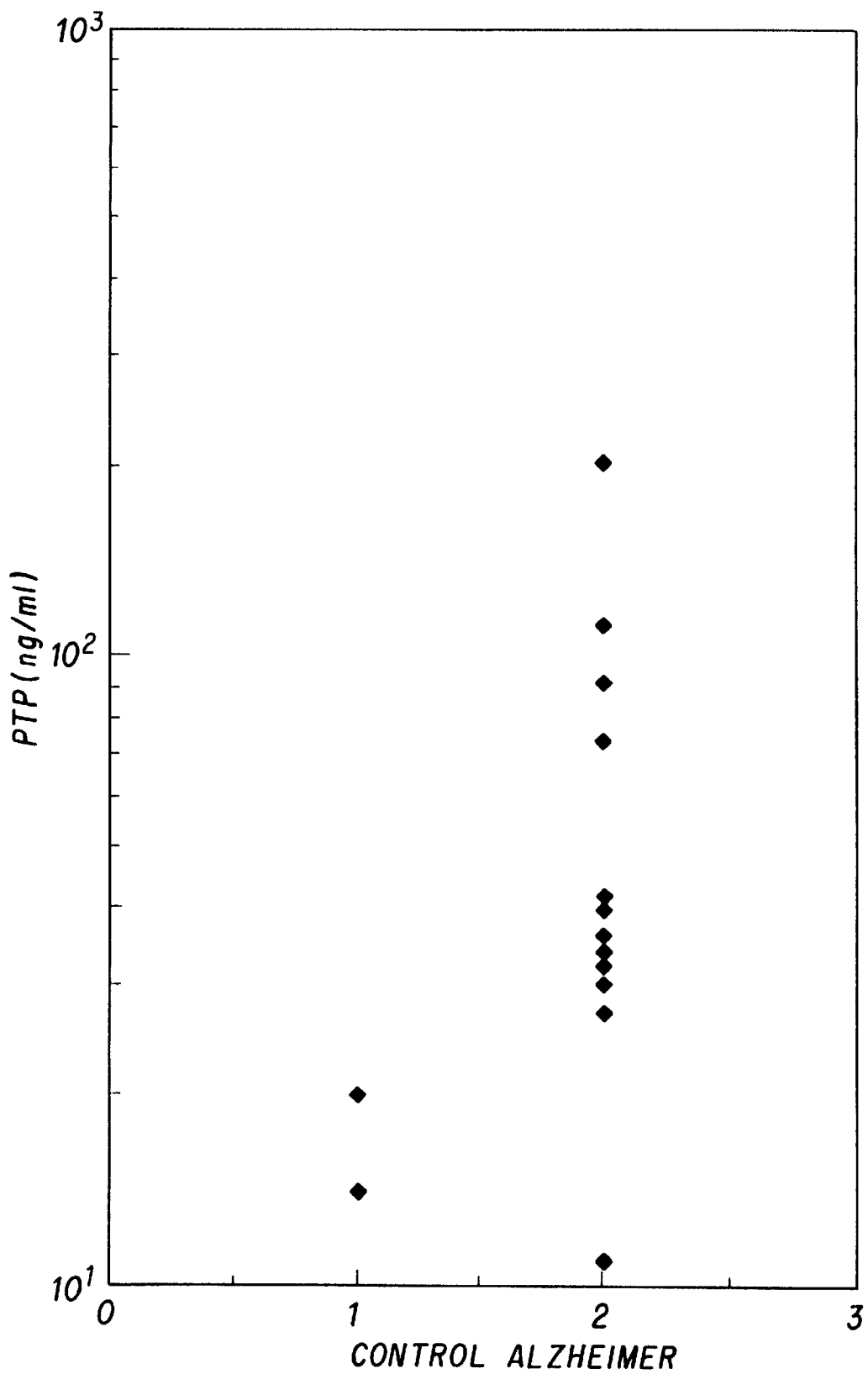
FIG. 7. Quantitative measurement of soluble nPTP levels in CSF derived from 12 subjects with AD compared to two normal control subjects. nPTP levels in CSF of some AD patients are strikingly elevated.

As shown in FIG. 7, nPTP CSF levels varied from 10 to 250 ng/ml. In 11/12 subjects, CSF levels were >20 ng/ml. Four AD patients had CSF concentrations that were found to be strikingly high (>150 ng/ml). These elevated CSF levels are paralleled by the findings described in AD brain tissue (FIGS. 1 and 3) with the same M-IRMA, and illustrates the value of this test in the diagnosis of this disease.

Figure 8:
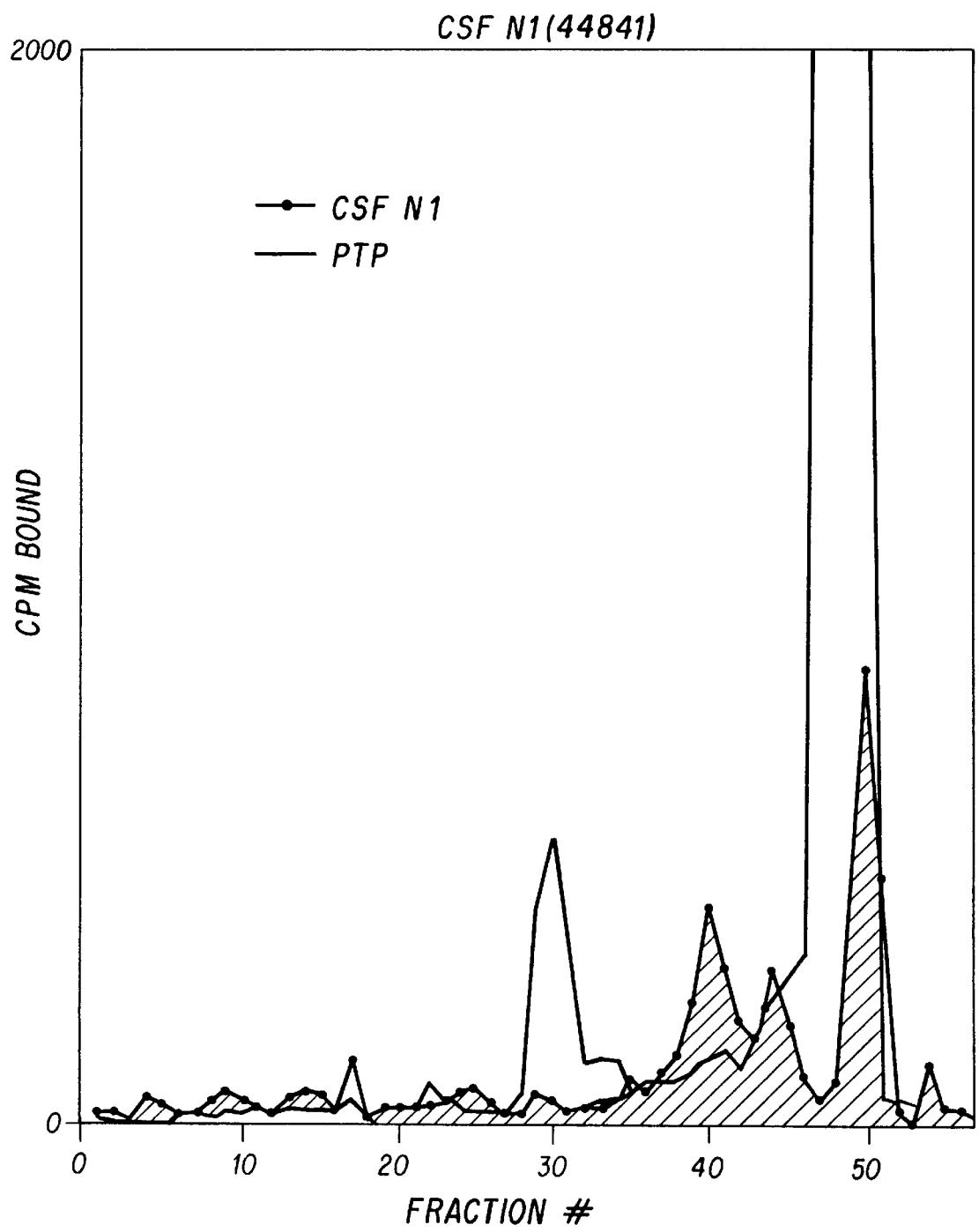
FIG. 8. Molecular sizes of nPTP in CSF derived from a patient with AD compared to PTP from pancreatic fluid. There are three peaks of immunoreactivity. One form (major peak) co-migrates with the pancreatic form of the protein. Two other smaller peaks with M.W. varying between 17 and 20 kD are also present (hatched areas).

When the inventors examined the molecular forms of nPTP in CSF from AD-afflicted subjects, as shown in FIG. 8, three species were observed. The most abundant form (hatched area) has the same molecular weight (14,000 daltons) as the native pancreatic PTP. There are two slightly larger molecular weight species that were present as well and have approximately the same molecular weight range (17,000–20,000 daltons) as the nPTP found in AD brain tissue.

EXAMPLE XIII

Detection of Elevated PTP Levels in Acute Pancreatic Injury

Immunoreactivity is detectable when PTP standards are diluted in normal serum, for example. It became of interest, therefore, to determine whether PTP was detectable in the serum of patients with acute pancreatic inflammatory disease. As shown in Table II, explorations of PTP levels in patients with acute pancreatitis and pancreatic pseudocysts indicate easily detectable PTP levels in serum. Serum PTP levels decreased following drainage of the acute inflammatory mass (pseudocyst patient). This three-site assay was therefore shown to be very helpful in distinguishing acute pancreatic disease from other acute intra-abdominal surgical emergencies. It is postulated that severe acute pancreatic inflammation may lead to the release of PTP from acinar cells into the circulation which is detectable using the methods described herein.

TABLE II

PTP Immunoreactivity in Serum by Monoclonal-based IRMA in Patients with Acute Pancreatic Inflammation Using mAbs 7, 9 and 10

| Category | Patient | CPM/200 µl |
|---|---|---|
| Normal controls | | 105 ± 60 |
| Acute pancreatitis | | |
| 1. | B.R. | 325 ± 16 |
| 2. | J.B. | 418 ± 32 |
| 3. | N.E. | 660 ± 31 |
| Pancreatic abscess | | |
| 1. | V.C. | 2,460 ± 200 |
| 2. | P.C. | 5,001 ± 1,000 |
| Pancreatic pseudocyst | | |
| (11/7) | R.E. (11/7) | 2,512 ± 400 |
| (11/8) | *R.E. (11/8) | 120 ± 15 |

*Serum level one day after removal and drainage of pseudocyst.

EXAMPLE XIV

Preparation of PTP DNA Probes

To explore the role of PTP expression in central nervous system disease, bovine pancreatic cDNA was cloned by screening a pancreatic cDNA library using polyclonal antibody to purified bovine PTP (Gross, J., et al., *Proc. Natl. Acad. Sci. USA* 82:5627–5631 (1986)). Initially, a bovine pancreatic cDNA library was screened since the measured concentration of PTP in pancreatic fluid was approximately $10^6$ times higher than that found in the normal brain or CSF and there is a high homology at the protein level between the human and bovine form of the pancreatic protein (Gross et al., *J. Clin. Invest.* 76:2115–2126 (1985)). Twenty-seven clones with insert sizes between 0.65 and 0.9 kB were identified, two of which (0.65 kB: 3-2 clone and 0.85 kB: 2-1 clone) were used to prepare probes for clone-to-clone Southern hybridization after EcoRI digestion. The 3-2 clone hybridized only with itself and was not studied further. The 2-1 clone hybridized with 20 of the other clones and was sequenced by the dideoxynucleotide chain termination method using T7 polymerase (Ausubel, FM, et al., *Current Protocols in Molecular Biology*, Wiley & Sons, New York, 1989, Chapter 7.4).

EXAMPLE XV

Analysis of Bovine PTP Clone

The 2-1 clone contained a 790 bp sequence corresponding to a single continuous open reading frame beginning with an initiating methionine codon in position 35 and terminating at a stop codon in position 560 (FIG. 9). A non-coding region comprised the remainder of the clone, and was followed by a polyadenylation signal, indicating that the cDNA contained a full-length transcript. The deduced amino acid sequence yielded a protein with a predicted molecular weight of 19.3 kD and a pI of 5.7. Between residues 38 and 164, the predicted amino acid sequence matched the known sequence of the A and B chains of bovine PTP (Gross, J., et al., *Proc. Natl. Acad. Sci. USA* 82:5627–5631 (1986)) with 98% identity. However, from the cDNA it appears that the A and B chains are synthesized as a single precursor molecule which is probably cleaved post-translationally between alanine and isoleucine at residue 139. Moreover, like many other secretory proteins, the PTP cDNA encodes a 36 amino acid hydrophobic leader sequence with a potential cleavage site between alanine and arginine at residue 34. The translated protein contains six potential phosphorylation sites, but no glycosylation motifs. Analysis of the deduced amino acid sequence of PTP by translation of the cDNA clone disclosed a 47% identity with both human and rat islet cell regeneration factor (Terazono, K., et al., *J. Biol. Chem.* 263:2111–2114 (1988)), including conservation of the relative positions of all seven cystine residues among the three proteins. However, the deduced amino acid sequence of the human islet cell regeneration factor is identical to the human PTP sequence as previously reported (Gross et al., *J. Clin. Invest.* 76:2115–2126 (1985)). The bovine PTP demonstrates a 58% homology with the human form of the protein.

EXAMPLE XVI

Tissue Expression of PTP Gene

Figure 10A:
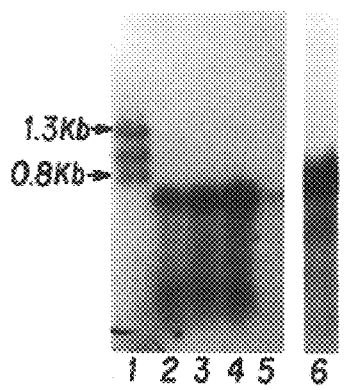
FIG. 10. PTP expression in bovine and human tissues. Total cellular RNA was extracted in 5M guanididium isothiaocyanate and pelleted through a 5.7 M CsCl cushion. The samples (10 μg each) were denatured, electrophoresed in a 1.2% agarose-formaldehyde gel and transferred to a nylon membrane (Nytran or Hybond). The filters were hybridized ovenight at 42° C. in buffer containing 50% formamide, 5×SSC, 5×Denhardt's solution, and 0.1% SDS using an EcoRI insert for the λZAP plasmid labeled with deoxycytidine 5'[α-$^{32}$P] triphosphate by the random priming method. The final washes were done in 0.2×SSC, 0.1% SDS at 60° C. 3'-end labeled Phi X174 digested with HaeIII and the positions of 18S and 28S ribosomal RNA were used as molecular weight markers (left).

PTP expression in bovine and human tissues was investigated by using Northern analysis and dot blot hybridization with total cellular RNA. A single 0.8 kB transcript was detected in both bovine and human pancreas (FIG. 10A, lanes 2–5). Using oligonucleotide probes specific for human PTP (FIG. 11), a 0.8 kB transcript was also seen in human pancreas (FIG. 10A, lane 6). By dot blot hybridization using 1 µg of RNA, the signal in bovine pancreas was strikingly higher than in human, and the signal in humans was several fold higher than in rat pancreas, suggesting some evolutionary conservation of the mRNA sequence. PTP transcripts were not detected in bovine kidney, liver, brain, salivary gland, lung, heart or skeletal muscle by Northern analysis. However, by dot blot hybridization, low levels of transcript were detected in kidney, salivary gland and brain but not the other tissues.

Figure 10B:
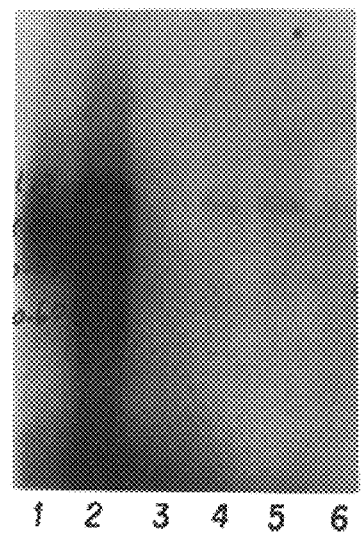
Figure 10C:

In human infant and adult brain, a single transcript of 1.3 kB was detected by Northern analysis (FIG. 10B, lane 5). By dot blot hybridization, the levels of PTP mRNA were approximately 10 fold higher in infant brain than in adult. In view of the increased immunoreactive PTP in AD brains (See Example I, Section C, above) the abundance of PTP mRNA was assessed in six patients with AD, and six age-matched controls. By dot blot hybridization using the human PTP specific oligonucleotide probes (FIG. 11), we observed a 5–10 fold increase in 5 of 6 individuals with AD (FIG. 10C, Lanes 7–12) compared with controls (FIG. 10C, lanes 1–6). Similar increases in PTP mRNA levels were observed in 2 of 3 patients with DS and AD lesions.

EXAMPLE XVII nPTP in the Human Nervous System During Development

A. Brain Tissue

The higher levels of PTP mRNA in infant compared with adult brains prompted an examination of nPTP immunoreactivity during development. Paraffin-embedded sections of brain from infants born prematurely at 24, 27, 29, 32, 34 and 36 weeks gestation and who died within the prenatal period, full-term infants who died at 1 or 6 months of age, and a 16-year-old, were simultaneously immunostained (along with tissue from aged controls, patients with AD and individuals with DS) with mAbs to human PTP (See Example I, above) by the avidin-biotin horseradish peroxidase complex method (see Example I, Section C, above).

At 24 weeks gestation, nPTP immunoreactivity was faint and restricted to neuritic processes in future grey matter structures. The intensity of nPTP immunoreactivity increased progressively as a function of age up to 6 months. For the most part, labeling was localized within the neuropil, although scattered individual and sample aggregates of neurons in the vicinity of focal ischemic damage manifested intense perikaryal immunoreactivity. Cerebral tissue from the 16 year old overall exhibited minimal PTP immunoreactivity, similar to brains from aged, neuropathologically intact controls (see FIGS. 5 and 6).

In infant brains of all ages, the choroid plexus and ependymal cells lining the ventricular system exhibited intense immunoreactivity for nPTP.

However, one finding of interest which may help explain in part the proposed biological function of PTP was the observations in a two-week-old embolic infarct; the neurons were necrotic and did not express nPTP, although the immunoreactivity in the neuropil was higher than that observed in more intact areas of brain. It was striking that in the immediately adjacent gyrus most of the neurons contained abundant immunoreactivity PTP within the perikarya and neuropil which is comprised of neuritic processes and extracellular space. Given the age of the infarct, it is concluded that neurons in the adjacent gyrus may have been sprouting into the injured zone. This finding suggests that PTP expression could be related to neuronal sprouting and regeneration in the mature CNS. This hypothesis finds support in the evidence that:

1) the levels of immunoreactive nPTP are higher in developing brains which are undergoing intense restructuring, compared with adult brains which remodel at much lower rates;
2) PTP mRNA levels are higher in the infant than in the adult brain;
3) homology is great between PTP and rat islet cell regeneration factor, and complete identity was found with a human islet cell regeneration factor (Reference 9).

B. Cerebrospinal Fluid (CSF)

The possibility of detecting PTP in CSF was tested by examining postmortem CSF specimens for immunoreactive PTP using a 3-site forward sandwich, antigen capture IRMA (described in Table I, above). Concentrations in normal CSF ranged from 10 to 30 ng/ml (n=5). The molecular weight of the CSF protein (17–20 kD) was greater than the pancreatic form (14 kD), characteristic of nPTP. Taken together with the larger transcript size of nPTP in the brain compared with PTP in the pancreas, these findings further indicate that nPTP, the CNS form of PTP, is larger than the pancreatic form, while sharing several cross-reactive epitopes.

C. Discussion

Combined with the information about its structural identity of the human PTP with islet cell regeneration factor, the high levels of PTP mRNA in the developing brain compared with the mature brain, and increased immunoreactivity in a setting of regenerative sprouting (for example, recent infarction), PTP in both the neural and pancreatic forms, is associated with cellular growth. However, our previous studies have demonstrated that the pancreatic form of the protein is found in great abundance in some but not all acinar cells of the exocrine pancreas and not in islet cells. Furthermore, the concentration of the protein found in pancreatic fluid is in the mg/ml range; a level unusually high for a growth factor.

DEPOSITS

Three hybridoma cell lines which respectively secrete mAb 7 (which cell line and antibody are equivalently designated as "TH-7-7-8"), mAb 9 (which cell line and antibody are equivalently designated as "TH-9-9-9"), and mAb 10 (which cell line and antibody are equivalently designated as "TH 110-11-9"), utilized in the present invention, were deposited on Dec. 21, 1988 at the American Type Culture Collection, Rockville, Md.

The following accession numbers were assigned to the cell lines:

| Cell Line   | Accession Number | mAb |
| ----------- | ---------------- | --- |
| TH 7-7-8    | HB 9934          | 7   |
| TH 9-9-9    | HB 9935          | 9   |
| TH 110-11-9 | HB 9936          | 10  |

MAbs 7, 9, and 10 may be prepared according to the method described in Gross et al., *J. Clin. Invest.* 76:2115–2126 (1985).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for detecting the presence of nPTP in a human subject, said method comprising:
   (a) contacting cerebrospinal fluid or brain tissue removed from said human subject with one or more antibodies that specifically bind PTP and nPTP; and (b) detecting any of said antibodies which are bound to, or detecting any of said antibodies which are not bound to, nPTP.

2. A method for detecting the presence of nPTP in a human fetus or embryo, said method comprising:
   (a) removing amniotic fluid from a female human pregnant with said fetus or embryo
   (b) contacting the amniotic fluid of (a) with one or more antibodies that specifically bind PTP and nPTP; and
   (c) detecting any of said antibodies which are bound to, or detecting any of said antibodies which are not bound to, nPTP.

3. The method of claim 2, wherein said method aids in the prenatal diagnosis of Down's Syndrome or a neural tube defect.

4. The method of claim 2, wherein said method aids in the prenatal diagnosis of Down's Syndrome in a human fetus or embryo, and wherein detection of at least approximately 20 ng/ml of nPTP indicates that said fetus or embryo has Down's Syndrome.

5. The method of claim 2, wherein said method aids in the prenatal diagnosis of a neural tube defect in a human fetus or embryo, and wherein detection of at least approximately 200 ng/ml of nPTP indicates that said fetus or embryo has a neural tube defect.

6. A method which aids in the diagnosis of Alzheimer's Disease in a human subject suspected of having Alzheimer's Disease which comprises:
   (a) incubating a biological sample comprising cerebrospinal fluid or brain tissue from said subject in the presence of an antibody that specifically binds PTP and nPTP; and
   (b) detecting any of said antibodies which are bound to, or detecting any of said antibodies which are not bound to, nPTP,
wherein detection of elevated levels of nPTP indicates that said subject has or should be further examined for other indications of Alzheimer's Disease.

7. The method of claim 6, wherein said incubating step further includes adding a known quantity of labeled PTP or nPTP whereby a competitive immunoassay is established.

8. The method of claim 7, wherein said label is capable of emitting radiation.

9. The method of claim 8, wherein said label is $^{125}$I.

10. A method which aids in the diagnosis of Down's Syndrome in a human subject suspected of having Down's Syndrome which comprises:
   (a) incubating a biological sample comprising cerebrospinal fluid or brain tissue from said subject in the presence of one or more antibodies that specifically bind PTP and nPTP;
   (b) detecting any of said antibodies which are bound to, or detecting any of said antibodies which are not bound to, nPTP in said sample; and
   (c) comparing the results obtained in step (b) with results obtained with samples comprising known concentrations of purified PTP or nPTP, in order to determine the concentration of nPTP in said sample,
wherein detection of at least approximately 20 ng/ml of nPTP in said sample indicates that said subject has Down's Syndrome.

11. The diagnostic method of claim 10, wherein said detection is by an immunometric assay.

12. The method of claim 11, wherein said immunometric assay is a monoclonal antibody-based immunometric assay.

13. The method of claim 11, wherein said immunometric assay comprises two different antibodies bound to a solid phase support combined with a third different detectably labeled antibody in solution.

14. The method of claim 10, wherein said incubating step further includes adding a known quantity of labeled PTP or nPTP whereby a competitive immunoassay is established.

15. The method of claim 14, wherein said label is capable of emitting radiation.

16. The method of claim 15, wherein said label is $^{125}$I.

17. A method which aids in the diagnosis of a neural tube defect in a human subject suspected of having a neural tube defect which comprises:
   (a) incubating a biological sample comprising cerebrospinal fluid or brain tissue from said subject which is suspected of containing elevated levels of nPTP, in the presence of one or more antibodies that specifically bind PTP and nPTP;
   (b) detecting any of said antibodies which are bound to, or detecting any of said antibodies which are not bound to, nPTP in said sample; and
   (c) comparing the results obtained in step (b) with results obtained with samples comprising known concentrations of purified PTP or nPTP, in order to determine the concentration of nPTP in said sample,
wherein detection of at least approximately 200 ng/ml of nPTP indicates that said subject has a neural tube defect.

18. The method of claim 17, wherein said detection is by an immunometric assay.

19. The method of claim 18, wherein said immunometric assay is a monoclonal antibody-based immunometric assay.

20. The method of claim 18, wherein said immunometric assay comprises two different antibodies bound to a solid phase support combined with a third different detectably labeled antibody in solution.

21. The method of claim 17, wherein said incubating step further includes adding a known quantity of labeled PTP nPTP whereby a competitive immunoassay is established.

22. The method of claim 21, wherein said label is capable of emitting radiation.

23. The method of claim 22, wherein said label is $^{125}$I.

24. A method which aids in the diagnosis of pancreatic disease or injury in a human subject suspected of having pancreatic disease or injury which comprises:
   (a) incubating a sample of urine from said subject suspected of containing elevated levels of PTP in the presence of one or more antibodies that specifically bind PTP;
   (b) detecting any of said antibodies which are bound to, or detecting any of said antibodies which are not bound to, PTP; and
   (c) comparing the results obtained in step (b) with results obtained with samples comprising known concentrations of purified PTP or NPTP, in order to determine the concentration of PTP in said sample,
wherein detection of at least approximately 150 ng/ml of PTP in said sample indicates that said subject suffers from pancreatic disease or injury.

25. The method of claim 24, wherein said detection is by an immunometric assay.

26. The method of claim 25, wherein said immunometric assay is a monoclonal antibody-based immunometric assay.

27. The method of claim 25, wherein said immunometric assay comprises two different antibodies bound to a solid phase support combined with a third different detectably labeled antibody in solution.

28. The method of claim 24, wherein said incubating step further includes adding a known quantity of labeled PTP or nPTP whereby a competitive immunoassay is established.

29. The method of claim 28, wherein said label is capable of emitting radiation.

30. The method of claim 29, wherein said label is $^{125}$I.

31. A method which aids in the diagnosis of Down's Syndrome in a human subject suspected of having Down's Syndrome which comprises:
   (a) incubating a biological sample comprising cerebrospinal fluid or brain tissue from said subject which is suspected of containing elevated levels of nPTP, in the presence of one or more antibodies that specifically bind PTP and nPTP; and
   (b) detecting any of said antibodies which are bound to, or detecting any of said antibodies which are not bound to, nPTP,
   wherein detection of elevated levels of nPTP indicates that said subject has or should be further examined for other indications of Down's Syndrome.

32. A method which aids in the diagnosis of a neural tube defect in a human subject suspected of having a neural tube defect which comprises:
   (a) incubating a biological sample comprising cerebrospinal fluid or brain tissue from said subject which is suspected of containing elevated levels of nPTP, in the presence of one or more antibodies capable of binding PTP and nPTP; and
   (b) detecting any of said antibodies which are bound to, or detecting any of said antibodies which are not bound to, NPTP,
wherein detection of elevated levels of nPTP indicates that said subject has or should be further examined for other indications of a neural tube defect.

33. A method for detecting the presence of nPTP in a human subject, said method comprising:
   (a) preparing a soluble extract of cerebrospinal fluid, brain tissue, blood, urine, lymph or serum from said human subject;
   (b) fractionating the soluble extract of (a) according to molecular size, and retaining fractions comprising material with an apparent molecular weight of from about 17 to about 20 kilodaltons;
   (c) contacting one or more of the fractions retained in (b) with one or more antibodies that specifically bind nPTP; and
   (d) detecting any of said bound antibodies which are bound to, or detecting any of said antibodies which are not bound to, nPTP.

34. A method which aids in the diagnosis of pancreatic or neural disease or injury in a human subject suspected of having pancreatic or neural disease or injury which comprises:
   (a) contacting cerebrospinal fluid, blood or lymph of said subject with one or more labeled antibodies that specifically bind nPTP and PTP; and
   (b) detecting by imaging any of said antibodies which are bound to PTP, nPTP or PTP and nPTP,
wherein the detection of an elevated level of PTP, nPTP or PTP and nPTP is performed by in situ imaging of said bound antibodies, and wherein detection of an elevated level of PTP, nPTP or PTP and nPTP indicates that said subject has or should be further examined for other indications of pancreatic or neural disease or injury.

35. A method which aids in the diagnosis of pancreatic or neural disease or injury in a human subject suspected of having pancreatic or neural disease or injury which comprises:
   (a) contacting cerebrospinal fluid, blood or lymph of said subject with one or more labeled antibodies that specifically bind nPTP and PTP; and
   (b) detecting by imaging any of said antibodies which are bound to PTP, nPTP or PTP and nPTP,
wherein the detection of an elevated level of PTP, nPTP or PTP and nPTP is performed by in vitro imaging of said bound antibodies, and wherein detection of an elevated level of PTP, nPTP or PTP and nPTP indicates that said subject has or should be further examined for other indications of pancreatic or neural disease or injury.

36. The method of claim 1, 2, 6, 7–23, 24–30, 33, 34 or 35, wherein said antibodies are selected from the group consisting of:
   (a) an antibody substantially free of natural impurities;
   (b) a monoclonal antibody; and
   (c) a fragment of (a) or (b) that specifically bind PTP and nPTP.

37. The method of claim 1, 2, 6, 31, 32, or 33, wherein said detection of PTP, nPTP or PTP and nPTP is performed by immunometric assay.

38. The method of claim 37, wherein said immunometric assay is a monoclonal antibody-based immunometric assay.

39. The method of claim 37, wherein said immunometric assay comprises two different antibodies bound to a solid phase support combined with a third different detectably labeled antibody in solution.

40. The method of claim 17, 3 or 5, wherein said neural tube defect is selected from the group consisting of:
   (a) anencephaly;
   (b) spina bifida;
   (c) meningocele;
   (d) meningomyelocele; and
   (e) holoprosencephaly.

41. The method of any one of claims 1, 2, 6, 7–23, 24–30, 33, 34, 35, wherein said antibodies are produced by a hybridoma deposited at the American Type Culture Collection selected from the group consisting of HB 9934, HB 9935, and HB 9936.

* * * * *